United States Patent [19]

Doggett

[11] Patent Number: 5,615,052
[45] Date of Patent: Mar. 25, 1997

[54] LASER DIODE/LENS ASSEMBLY

[75] Inventor: David E. Doggett, Sunnyvale, Calif.

[73] Assignee: Bruce W. McCaul, Palo Alto, Calif.

[21] Appl. No.: 332,991

[22] Filed: Nov. 1, 1994

Related U.S. Application Data

[63] Continuation-in-part of Ser. No. 48,611, Apr. 16, 1993, Pat. No. 5,500,768.

[51] Int. Cl.$^6$ ......................................... H01S 3/19
[52] U.S. Cl. ............................... 359/811; 359/642
[58] Field of Search ................................ 359/642, 811; 372/34, 36, 101

[56] References Cited

U.S. PATENT DOCUMENTS

| | | | |
|---|---|---|---|
| 3,829,694 | 8/1974 | Goto | 250/339 |
| 3,995,960 | 12/1976 | Fletcher et al. | 356/204 |
| 4,068,125 | 1/1978 | Bell | 250/340 |

(List continued on next page.)

FOREIGN PATENT DOCUMENTS

| | | |
|---|---|---|
| 4122572A1 | 1/1993 | Germany . |
| WO90/00732 | 1/1990 | WIPO . |

OTHER PUBLICATIONS

Philip C. Hobbs, "Research Report: Shot Noise Limited Optical Measurements at Baseband With Noisy Lasers", IBM Research Division, Engineering Technology RC 16199 (#71972) Oct. 17, 1990, 27 pgs.

R.J. Smith et al., "Dart: A Novel Sensor For Helicopter Flight Safety", Photonics Spectra, Jul. 1992, pp. 110–116.

Combitech Group Saab Missiles, Saab Diodair 2000 Data Sheet, "Laser Sensor System for in situ measurement of oxygen", 1 pg.

Combitech Group Saab Missiles, Saab Diodair 2000 Data Sheet, "Laser Sensor System for On–line Gas Monitoring", 4 pgs.

M. Bobb, "Diode–Laser Collimators Suit Communication Applications In Space", Laser Focus/Electro–Optics, p. 79.

David S. Bomse et al., "Frequency modulation and wavelength modulation spectroscopies: comparison of experimental methods using a lead–salt diode laser", Applied Optics, vol. 31, No. 6, Feb. 20, 1992, pp. 718–731.

Daniel T. Cassidy, "Trace gas detection using 1.3 μm InGaAsP diode laser transmitter modules", Applied Optics, vol. 27, No. 3, Feb. 1, 1988, pp. 610–614.

"Characteristics of Laser Diodes", Optics Guide V—Melles Griot Supply Catalog, 1990, pp. 9–35.

Optima Precision, Inc. Price List, Jun. 1991, 1 pg.

Schematic Diagram of Aspheric Plastic Lens, Optima Precision, Inc., Jan./Feb. 1990, 3 pgs.

Optima Precision, Inc., Specification sheet, Jul. 1987, 1 pg.

"Laser Diode Collimators", D.O. Industries Specification sheet, pp. 2–8.

(List continued on next page.)

Primary Examiner—Scott J. Sugarman
Attorney, Agent, or Firm—Skjerven, Morrill, MacPherson, Franklin and Friel; T. Lester Wallace

[57] ABSTRACT

A laser diode/lens assembly wherein a lens (or multi-lens assembly) is immovably adhered to a housing of a laser diode package. The laser diode package may be a metal can style package having a substantially transparent window portion through which laser radiation is emitted when a laser diode inside the housing is supplied with current. The lens may be immovably fixed to an outer surface of this window so that a central axis of a beam of laser radiation emerging from the lens has a desired spatial relationship with a reference surface of the housing. An adhesive such as an epoxy adhesive which is cured under exposure to ultraviolet radiation may be used to freeze the lens in place to the window when the lens is correctly positioned. In accordance with some embodiments of the present invention, a lens is positioned in three dimensions (X, Y and Z) and then fixed in three dimensional space with respect to a laser diode housing. Fixing the position of the lens in the Z dimension at a desired location allows the focal point of the laser diode/lens assembly to be set so as not to focus laser radiation on a window of a gas spectroscopy device.

18 Claims, 14 Drawing Sheets

U.S. PATENT DOCUMENTS

| | | | |
|---|---|---|---|
| 4,084,906 | 4/1978 | Bibbero | 356/96 |
| 4,410,273 | 10/1983 | Mantz et al. | 356/319 |
| 4,489,239 | 12/1984 | Grant et al. | 250/339 |
| 4,492,862 | 1/1985 | Grynberg et al. | 250/255 |
| 4,498,737 | 2/1985 | Doggett | 350/237 |
| 4,553,238 | 11/1985 | Shaw et al. | 372/6 |
| 4,557,603 | 12/1985 | Oehler et al. | 356/418 |
| 4,684,258 | 8/1987 | Webster | 356/409 |
| 4,684,805 | 8/1987 | Lee et al. | 250/343 |
| 4,730,112 | 3/1988 | Wong | 250/343 |
| 4,748,632 | 5/1988 | Preston | 372/32 |
| 4,780,613 | 10/1988 | Berstein et al. | 250/343 |
| 4,800,886 | 1/1989 | Nestor | 128/634 |
| 4,849,637 | 7/1989 | Cerff et al. | 250/345 |
| 4,883,963 | 11/1989 | Kemeny et al. | 250/339 |
| 4,886,358 | 12/1989 | Pellenbarg et al. | 356/301 |
| 4,901,325 | 2/1990 | Kato et al. | 372/44 |
| 4,924,095 | 5/1990 | Swanson, Jr. | 250/338.5 |
| 4,934,816 | 6/1990 | Silver et al. | 356/409 |
| 4,937,448 | 6/1990 | Mantz et al. | 250/343 |
| 4,968,887 | 11/1990 | Wong | 250/343 |
| 4,969,702 | 11/1990 | Anderson | 350/96.2 |
| 5,032,435 | 7/1991 | Biefeld et al. | 427/8 |
| 5,047,639 | 9/1991 | Wong | 250/341 |
| 5,061,857 | 10/1991 | Thompson et al. | 250/458.1 |
| 5,094,819 | 3/1992 | Yager et al. | 422/82.07 |
| 5,096,671 | 3/1992 | Kane et al. | 422/82.07 |
| 5,124,130 | 6/1992 | Costello et al. | 422/82.06 |
| 5,146,294 | 9/1992 | Grisar et al. | 356/435 |
| 5,173,749 | 12/1992 | Tell et al. | 356/437 |

OTHER PUBLICATIONS

Siemens Optoelectronics Data Book, 1990, 2 pgs.

Diverse Optics, Inc., Specification sheet, 3 pgs.

Mitsubishi Optoelectronics Data Book, Mitsubishi Electric, 1990, pp. 3–12 to 3–15.

J. Snyder, et al., "Cylindrical microlenses improve laser–diode beams", Laser Focus World, Feb. 1993, pp. 97–99.

J. Snyder, et al., "Fast, inexpensive, diffraction limited cylindrical microlenses", SPIE Proceedings Reprint vol. 1544, Miniature and Micro–Optics Fabrication and System Applications, 1991, pp. 146–151.

Blue Sky Research Data sheet, "New High–Efficiency Fiber Coupling Concepts" 1993, 3 pages.

Blue Sky Research Data sheet, "Virtual Point Source Optics For Laser Diodes" Sep. 1992, 1 pg.

Blue Sky Research Price Sheet, 1992, 1 pg.

Blue Sky Research Data sheet, "SAC Series μlens™ Single Axis Collimator", Mar. 1993, 1 pg.

J. Snyder, et al., "Fast diffraction–limited cylindrical microlenses", Applied Optics, vol. 30, No. 19, 1 Jul. 1991, pp. 2743–2747.

Optima Precision, Inc. Data sheet, "Laser Diode Collimating and Objective Lens", May 1991, 2 pgs.

Optima Precision, Inc. Data sheet, "Collimated Diode Lasers and Mounting Kit", May 1991, 2 pgs.

H. Ahlberg et al., "IR–Laser Spectroscopy For Measurement Applications In The Industrial Environment", Institute of Electrical Measurements TR 85170, Chalmers University of Technology, Göteborg, Sweden, Dec. 1985, 8 pgs.

S. Lundqvist, et al., "Measurements of pressure–broadening coefficients of NO and $O_3$ using a computerized tunable diode laser spectroscopy", Applied Optics vol. 21, No. 17, Sep. 1, 1982, pp. 3109–3113.

R.S. Eng, et al., "Tunable diode laser spectroscopy: an invited review", Optical Engineering, vol. 19, No. 6, Nov./Dec. 1980, pp. 945–960.

Nipon Electric Glass America, Inc. data sheet for "Lenslet" Lens for Optical Module, Ref. No. 9310–26E, 2 pgs.

S. Höjer et al., "Measurements of electric field strength in gas insulated high–voltage components using infrared diode laser absorption spectroscopy", Applied Optics, vol. 25, No. 17, 1 Sep. 1986, pp. 2984–2987.

Combitech Group Saab Missiles, Saab Diodair 2000 Data Sheet, "Laser Sensor System for in situ measurement of ammonia", 1 pg.

J. Silver, "Frequency–modulation spectroscopy for trace species detection: theory and comparison among experimental methods", Applied Optics, vol. 31, No. 6, 20 Feb. 1992, pp. 707–717.

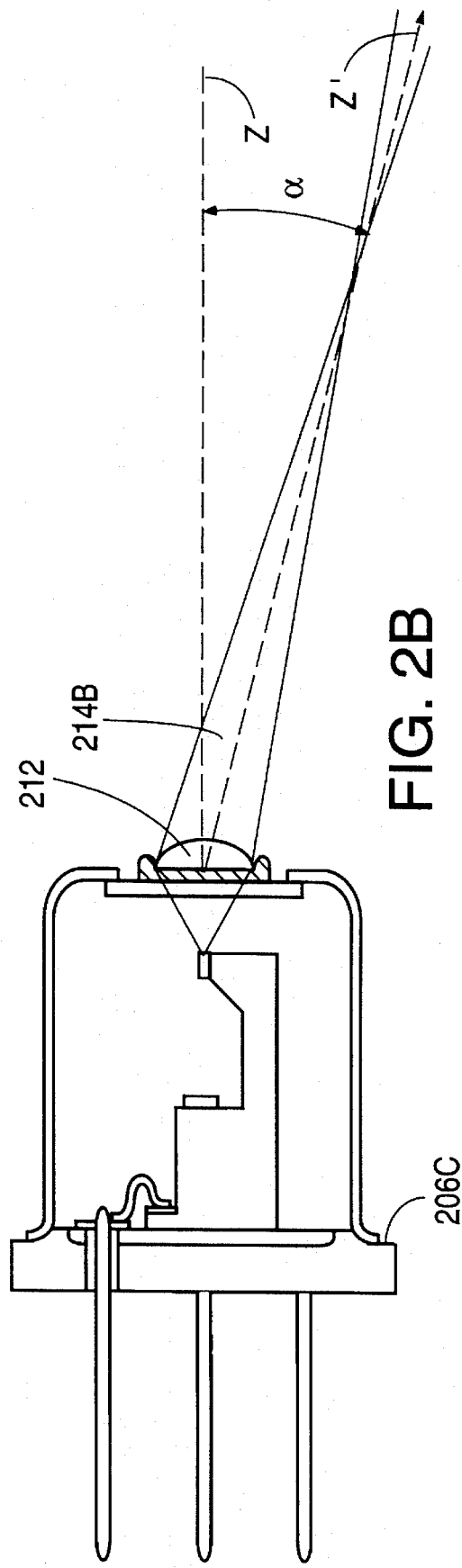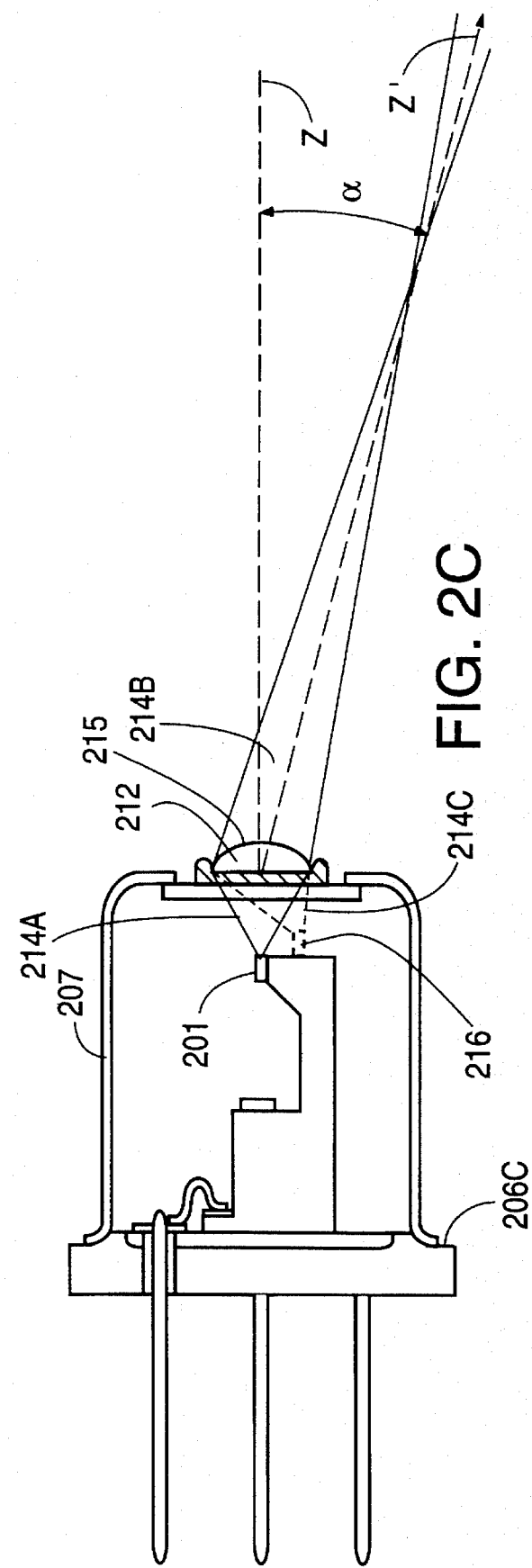

LASER DIODE/LENS ASSEMBLY

CROSS REFERENCE TO RELATED APPLICATIONS

This application is a continuation-in-part of U.S. application Ser. No. 08/048,611, filed Apr. 16, 1993, entitled "LASER DIODE/LENS ASSEMBLY" now U.S. Pat. No. 5,500,768, the subject matter of which is incorporated herein by reference.

FIELD OF THE INVENTION

This invention relates to a laser diode/lens assembly and a method of fabricating a laser diode/lens assembly. More particularly, this invention relates to a laser diode/lens assembly for use in laser gas spectroscopy.

BACKGROUND INFORMATION

Molecules of different gases have different electromagnetic radiation adsorption characteristics. A gas consisting of a given gas molecule therefore has a unique radiation adsorption spectrum. In one type of spectroscopic measurement of gases, the frequency of a radiation source is scanned over a defined frequency range, the resulting radiation is passed through a sample of a gas so that some of the radiation is absorbed by the gas, and the radiation which emerges from the gas sample is detected. The detected radiation may, for example, be indicative of such properties of the sample gas as gas concentration, gas composition, gas pressure and gas temperature.

Laser diodes are commonly used as a radiation source in gas spectroscopic devices to generate electromagnetic radiation of a single frequency and of a narrow linewidth. Laser radiation emitted from the exit aperture of a laser diode at the semiconductor chip surface, however, typically has a wide angle of divergence. As a consequence, the intensity of laser radiation incident on an object decreases rapidly as the object is placed farther and farther away from the laser diode. To reduce this decrease in intensity, it is desirable to reduce the divergence of the radiation emitted from a laser diode so that an adequate amount of laser radiation can be detected after the laser radiation has passed through the sample gas.

Many laser diode "collimator" configurations have been developed. One type of conventional laser diode "collimator" involves one or more lenses which receive the diverging radiation from the laser diode and collimate that radiation into a beam. The distance between the laser diode and the lenses must be controlled accurately or the beam will either focus or diverge. Due to tight mechanical tolerances required to produce a precisely collimated beam, conventional laser diode collimators typically have a lens focussing mechanism for adjusting the distance between the lens and the laser diode so that a desired degree of divergence or focus can be set and maintained. One such device is disclosed in FIG. 1 of U.S. Pat. No. 4,498,737 where precision adjustment of the laser diode to lens distance is accomplished through use of a threaded screw 4.

FIG. 1A (Prior Art) shows a second laser diode collimator of the prior art. A laser diode semiconductor chip 1A and lens 2A are contained in cylindrical supporting package 3A. The positioning of lens 2A in the X–Y plane relative to radiation emitted from the laser diode determines the direction beam 4A will point when it emerges from the lens. Lens 2A is, however, substantially fixed in the X–Y plane by the structure of the collimator package. The positioning of lens 2A in the Z dimension relative to the laser diode, determines whether beam 4A emerging from the lens is divergent, collimated, or focussed. The distance between lens 2A and laser diode 1A can be adjusted by rotating focus screw 5A. Once the lens is positioned in the Z dimension as desired, the lens is locked in place by locking screw 6A. When current is supplied to laser diode chip 1A on leads 7A and 8A, diverging laser radiation 10A is emitted from laser diode 1A. This radiation passes through transparent window 9A, and is redirected by lens 2A into laser beam 4A of a controlled divergence.

Due to their adjustability, however, such prior art laser diode collimators are susceptible to disalignment and decalibration problems. Physical shocks, physical vibrations, and forces resulting from temperature changes and pressure changes may cause the lens to move with respect to the laser diode. As a result, the relative divergence or focus as well as the pointing direction of beam 4A changes thereby resulting in spatial changes in the incident radiation on an object positioned at a given distance from the lens. Moreover, providing an adjustment and lens locking mechanism such as is shown in FIG. 1A adds complexity, size and significant expense to the collimator.

FIG. 1B (Prior Art) shows another type of collimator known in the prior art which sacrifices X–Y adjustability in order to reduce complexity. One such structure is offered by Diverse Optics of San Dimas, Calif. This type of collimator, however, does involve a mechanism for adjusting the distance between the laser diode 1B and the lens 2B so that the exit beam 4B can be precisely adjusted to produce a predefined divergence. Collimating lens 2B is mounted in plastic package 11B that is designed to mount tightly over a commonly available laser diode housing 12B. The plastic package is designed to slide with frictional resistance down cylindrical outer surface 13B of the laser diode housing 12B until the desired laser diode to lens distance in the Z dimension is achieved as evidenced by the character of the exit beam 4B. Upon observance of the proper exit beam divergence, adjustment is stopped and the tight fit of the plastic package in contact with outer surface 13B of the housing in area 14B insures that the lens 2B within the plastic package lib will maintain the desired laser diode to lens distance and therefore will continue to produce an exit beam of the desired divergence. Because the structure of FIG. 1B does not provide fore accurate adjustment of the lens in the X–Y plane, the direction in which the exit beam 4B points is variable and is governed by the accuracy of the mounting of lens 2B in plastic package 11B as well as the centering accuracy of laser diode chip 1B with respect to cylindrical diode housing 12B.

SUMMARY OF THE INVENTION

The present invention involves a laser diode/lens assembly wherein a lens or lens assembly is mounted directly to a housing containing a laser diode in such a way that a set, predetermined angular relationship is achieved between a reference surface of the housing and a central axis of a beam of laser radiation emerging from the lens or lens assembly. Once the lens or lens assembly is immovably fixed to the housing, the divergence or focus of the beam emerging from the laser diode/lens assembly cannot be further adjusted. Furthermore, the divergence or focus of one particular laser diode/lens assembly may be different than the divergence or focus of another laser diode/lens assembly, depending on the mechanical tolerances of the various parts making up the two different assemblies. After a particular lens or lens assembly is fixed to a particular laser diode housing, however, the magnitude of divergence or focus of that particular laser diode/lens assembly remains substantially constant even when the assembly is subjected to significant physical shocks, physical vibrations, temperatures changes and/or pressure changes.

In some applications, such as some gas spectroscopy applications, a beam of laser radiation is desired, the divergence or focus of which need not be precisely determined. The divergence or focus must, however, remain substantially constant during operation of the gas spectroscopy device due to the spatial variation in sensitivity of photodetectors as well as the spatial sensitivity of the beam directing properties of the sample cell containing the gas being analyzed. The relative divergence or focus of the laser beam must therefore remain constant so that a change in beam divergence or focus does not result in a variation in the detected intensity of radiation. Variations in the detected intensity of radiation at the detector due to lens movement may be erroneously interpreted as a change in the adsorption characteristics of the sample gas. The beam of laser radiation passing through the sample gas need not, however, be precisely collimated. By immovably fixing the lens with respect to the laser diode, the present invention avoids the decalibration problems associated with adjustment and locking mechanisms. Because the lens is immovably fixed directly to the housing of the laser diode, the divergence or focus of the laser beam, while not precisely known, varies less than does the divergence or focus of a beam typically emitted from a laser diode collimator of the prior art.

In accordance with some embodiments of the present invention, an X–Y plane and an orthogonal reference axis Z (reference axis Z is orthogonal to the X–Y plane) are defined with respect to a reference surface of the laser diode housing. A lens is adjusted and then permanently fixed in the X–Y plane in such as way that a predetermined angular relationship exists between the reference axis Z and the central axis of the beam of laser radiation emerging from the lens. The positioning of the lens with respect to the laser diode along reference axis Z is not precisely controlled. Accordingly, a highly collimated beam is not always produced by the laser diode/lens assembly. The beam exiting may be somewhat divergent or somewhat focussed. Indeed, it is desirable in some systems to select the focal length of the lens such that either a divergence or a focus condition exists even though the specific divergence or focus parameters are not tightly reproducible from assembly to assembly.

In some embodiments of the present invention, a laser diode is contained within a metal can style laser diode housing having a base portion, having a metal can portion mounted on the base portion, and having a substantially transparent window portion in the metal can portion through which laser radiation passes when the laser diode inside the housing is supplied with an electrical current. Commercially available laser diode housings of this type are available from a number of sources such as the laser type ML 4405 from Mitsubishi Electric Corp. of Tokyo, Japan. Laser diode housings of this type typically have a plurality of surfaces that can be utilized as reference surfaces for assembly purposes. In some embodiments of the present invention, a lens is adhered directly to a metal can portion of a laser diode housing so that a central axis of a beam of laser radiation emerging from said lens is substantially parallel to or collinear with a central axis of the cylindrical surface of a base portion of the laser diode housing.

A method for fixing a lens in relation to a laser diode inside a housing is also disclosed wherein a lens is placed in an amount of uncured adhesive disposed on the housing. The lens is then positioned in the uncured adhesive so that the central axis of a beam of laser radiation emerging from the lens has a predetermined angular relationship with respect to a reference surface of the housing. Once the lens is properly positioned, the adhesive is cured so that the lens is immovably fixed directly to the housing. In some embodiments, the adhesive is an epoxy which is cured after positioning of the lens by exposing the epoxy to ultraviolet radiation. The adhesive is substantially transparent to the laser light in embodiments where the adhesive fills a volume between the lens and the window portion of the housing.

In accordance with other embodiments of the present invention, a lens is positioned and then fixed in three dimensional space with respect to a laser diode housing. Fixing the position of the lens in the Z dimension at a desired position allows the focal point of the laser diode/lens assembly to be set so as not to focus laser radiation on a window of a gas spectroscopy device.

BRIEF DESCRIPTION OF THE DRAWINGS

FIGS. 2B and 2C are cross-sectional side views of an embodiment in accordance with the present invention wherein a beam is redirected by a lens fixed to a laser diode housing such that the beam emerging from the lens is not aligned to be parallel with a Z reference axis of the laser diode housing.

DETAILED DESCRIPTION OF THE PREFERRED EMBODIMENTS

Figure 1A:
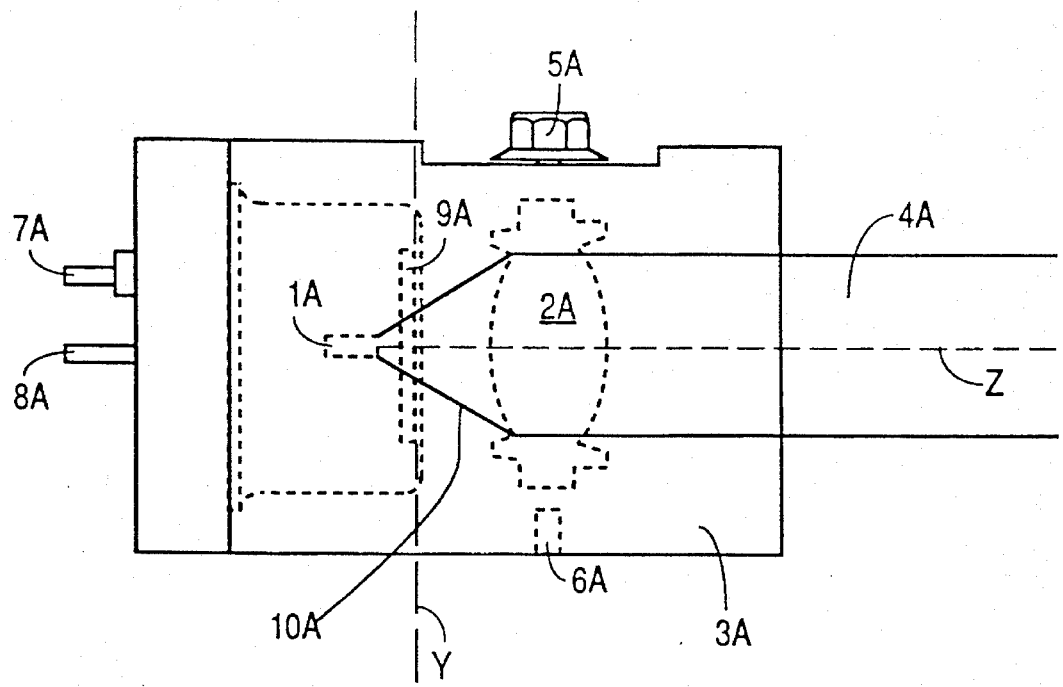
FIG. 1A (PRIOR ART) is a view of a conventional collimator and laser diode assembly.
Figure 1B:
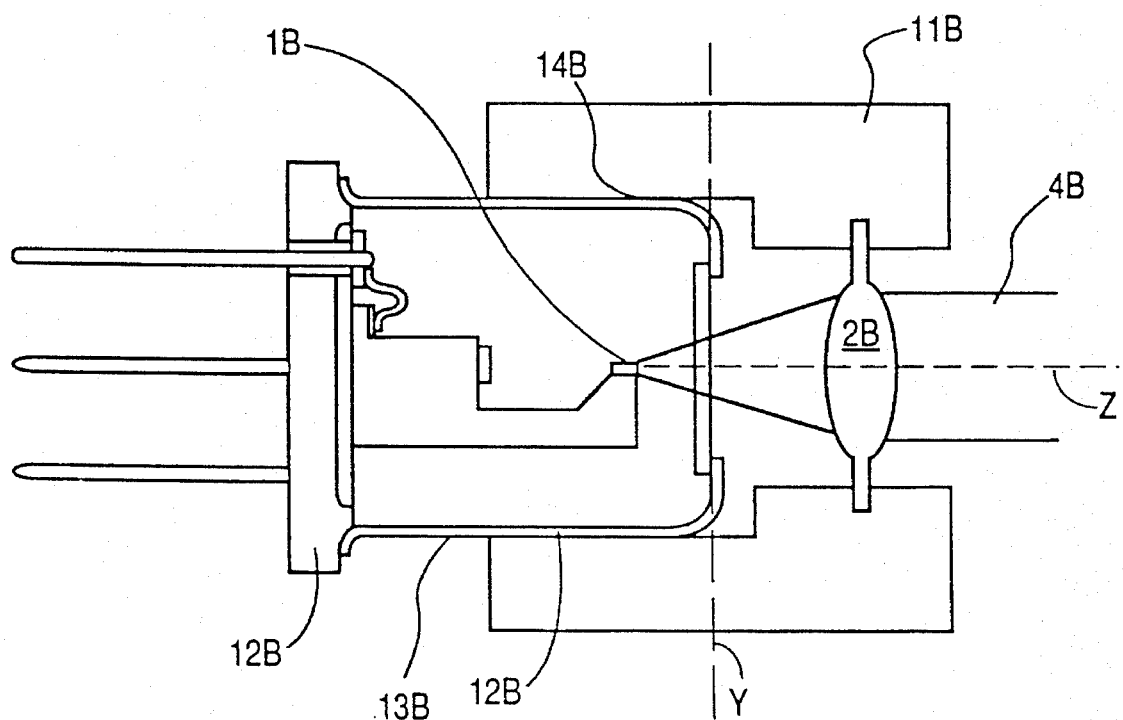
FIG. 1B (PRIOR ART) is a cross-sectional view of another conventional collimator and laser diode assembly.
Figure 2A:
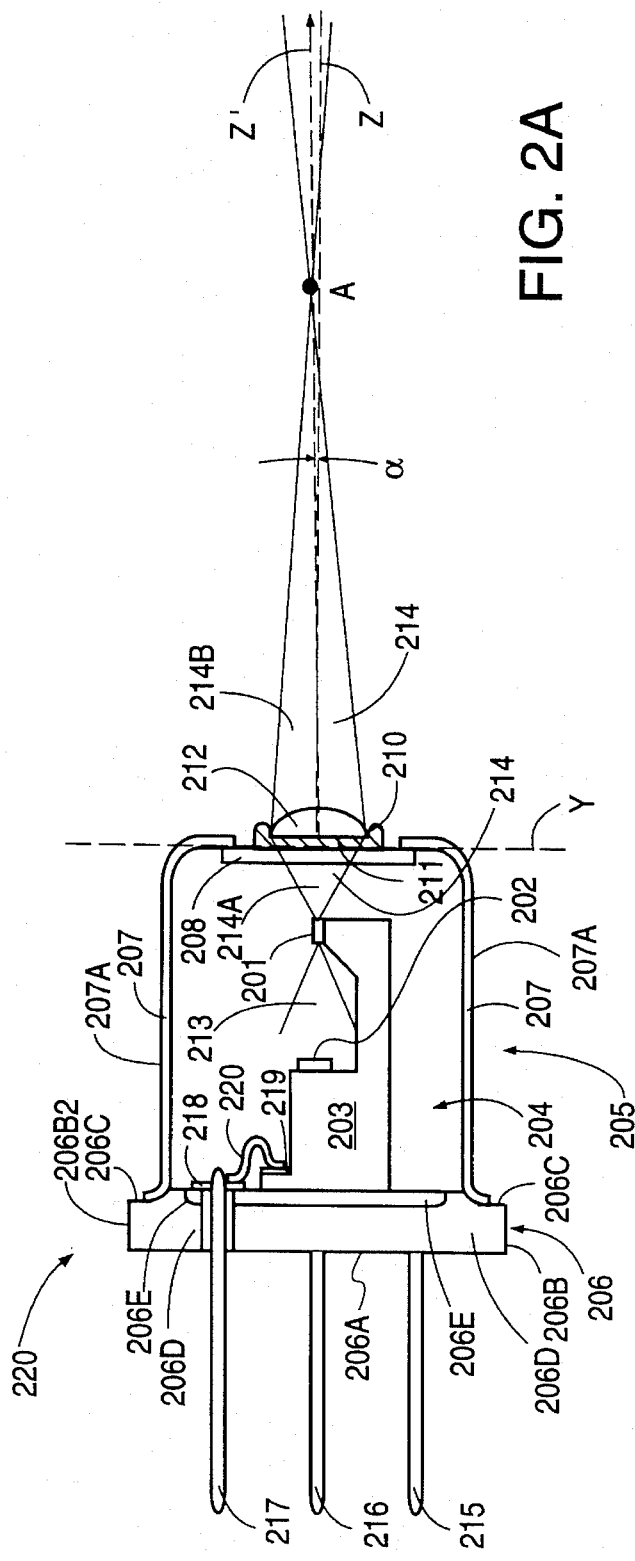
FIG. 2A is a cross-sectional side view of one embodiment of the present invention.
Figure 3:
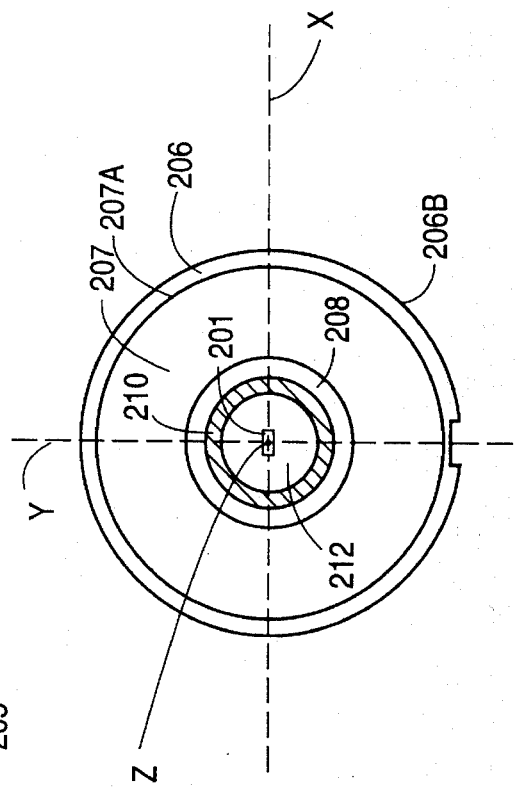
FIG. 3 is a top down view of the embodiment of FIG. 2A.

FIG. 2A is a cross-sectional side view of one embodiment of the present invention. FIG. 3 is a top down view of the embodiment of FIG. 2. A laser diode 201 and a photodetector 202 are mounted on a pedestal 203 inside a cavity 204. Cavity 204 may or may not be hermetically sealed. Cavity 204 is formed within housing 205 such as the TO-18 metal can style leaded package shown in FIG. 2A. In the embodiment shown in FIG. 2A, housing 205 comprises base portion 206, metal can portion 207, and a window portion 208 which is substantially transparent to the radiation emitted by laser diode 201. Base portion 206 has a circular and planar bottom surface 206A, a cylindrical side surface 206B, as well as a ledge surface 206C. Metal can portion 207 is welded, soldered, adhered, crimped or otherwise secured to base member 206. Window 208 may be secured to metal can portion 207 by welding, by pressure fitting or by an adhesive. An amount of adhesive 210 secures the substantially planar surface 211 of lens 212 to an outer surface of window portion 208. Planar surface 211 of lens 212 is disposed substantially parallel to an X-Y plane formed by this outer surface of window portion 208. This X-Y plane is substantially parallel to the housing reference surfaces 206A or 206C as indicated in FIGS. 2A and 3. Lens 212 may, for example, be an inexpensive glass spherical lens such as a 2.5 mm diameter, 2.0 mm focal length lens part number A43,398 manufactured by Edmund Scientific of Barrington, N.J. 08007.

Laser diode 201 inside cavity 204 emits two beams of laser radiation 213 and 214. Beam 213 is incident on photodetector 202 so that photodetector 202 outputs a signal indicative of the intensity of beam 213. Because beam 213 is emitted from the same semiconductor laser diode chip as is beam 214, the signal output by photodetector 202 is also indicative of the intensity of beam 214. That portion of beam 214 that is divergent inside housing 205 is designated as beam 214A. Beam 214 passes through window portion 208, passes through adhesive 210, and is directed by lens 212 to become the portion of beam 214 which is designated in FIG. 2A as beam 214B. Beam 214B is directed by lens 212 to point in the direction of central axis Z'. Lens 212 is adjusted in the X-Y plane so that central axis Z' of beam 214B is within a certain desired angle α with respect to reference axis Z. In the preferred embodiment the angle α is substantially zero so that central axis Z' of beam 214B is substantially parallel to or collinear with reference axis Z. In the embodiment shown in FIG. 2A, lens 212 focuses beam 214B at a point A. Lens 212 may, however, collimate beam 214B or leave beam 214B radiationally divergent.

It is possible that in certain embodiments an adjustment of central axis Z' to an angle α that is significantly divergent from reference axis Z would be desirable. Such a configuration is shown in FIG. 2B where beam 214B is directed at an angle α to reference axis Z where angle α is substantially different from zero. A reason for adjusting the output beam to point in a direction which is not orthogonal to reference plane X-Y, could be related to simple priority requirements of the ancillary apparatus associated with the particular use of radiation beam 214B or it could be a trade off necessitated by reflection from lens 212 where the lens 212 directs unwanted radiation back into laser diode 1. Moving lens 212 laterally would cause reflected radiation to concentrate at a point away from the output point of the laser diode. This would improve laser mode stability.

FIG. 2C shows how a lens that is positioned to direct beam 214B at a substantial angle α to reference axis Z will also direct beam 214A, reflected from spherical surface 215 to become beam 214C, in such a manner that the lens concentrates the reflected radiation at a point 216 which is not associated with the active region of laser diode 201. Such unwanted reflected radiation that enters the active region of laser diode 201 can cause laser diode 201 to become unstable in its operation and thereby to operate in such a way as to decrease the accuracy of the apparatus of which it is a part.

In the preferred embodiment, surface 206C is the reference surface and reference axis Z is a line orthogonal to surface 206C. It is to be understood, however, that other surfaces of a laser diode housing may be chosen as the reference surface. If, for example, the planar bottom surface 206A of base portion 206 is used as the reference surface, reference axis Z may be chosen to be a line orthogonal to planar surface 206A. Central axis Z' of beam 214B would then be oriented to be substantially parallel to or substantially collinear with this reference axis Z. Numerous laser diode housings other than the metal can style package of FIG. 2A could be used which would also provide their respective other particular reference surfaces.

Numerous interconnection schemes may be employed to connect the laser diode to a source of electrical current. In the specific embodiment shown in FIG. 2A, laser diode 201 has two terminals. Photodetector 202 also has two terminals. One of the terminals of laser diode 201 and one of the terminals of photodetector 202 may be connected together inside housing 205 so that only three leads, a diode lead 215, a photodetector lead 216 and a common lead 217, are required to form connections to the diode and photodetector inside the housing. Each of these leads extends from outside the housing, through a respective hole in a metal layer 206D of the base portion, through a respective hole in an insulator layer 206E of the base portion, and to a respective bonding pad on an interior surface of the base portion. Only common lead 217 is present in the plane of the cross-sectional view of FIG. 2A, so only common lead 217 is shown extending through base portion 206 in FIG. 2A.

In the embodiment shown in FIG. 2A, pedestal 203 has three bonding pads, one for connection to diode lead 215, one for connection to photodetector lead 216, and one for connection to common lead 217. Three wires are therefore provided to connect the common bonding pad of the pedestal to a corresponding bonding pad of the common lead, to connect the diode bonding pad of the pedestal to a corresponding bonding pad of the diode lead, and to connect the photodetector bonding pad of the pedestal to a corresponding bonding pad of the photodetector lead. FIG. 2A shows common lead 217 extending through base portion 206 and connecting to the bonding pad 218 of the common lead. A wire 220 is shown connecting this bonding pad 218 to a corresponding bonding pad 219 on pedestal 203. Connections disposed on the pedestal (not shown) connect appropriate bonding pads of the pedestal to appropriate terminals of the diode and the photodetector. Accordingly, current can be supplied to laser diode 201 via leads 215 and 217. Similarly, a signal indicative of the intensity of beam 214 is output by photodetector 202 on leads 216 and 217.

Because the beam of radiation emitted by a laser diode typically has a large divergence angle such as, for example, 35 degrees half angle, placement of lens 212 close to laser diode 201 allows the use of a small and inexpensive lens 212 to redirect substantially all of the laser radiation into beam 214B. The present invention therefore may be manufactured at significant cost savings in comparison to conventional assemblies wherein larger and more expensive lenses are placed farther away from the laser diode. The close placement of the lens to the laser diode also allows the creation of a smaller diameter laser beam without having to resort to beam reduction telescopes. In some embodiments, lens 212 has a diameter of approximately 1 to 9 mm and is disposed approximately 0 to 4 mm from the laser diode.

Figure 4A:
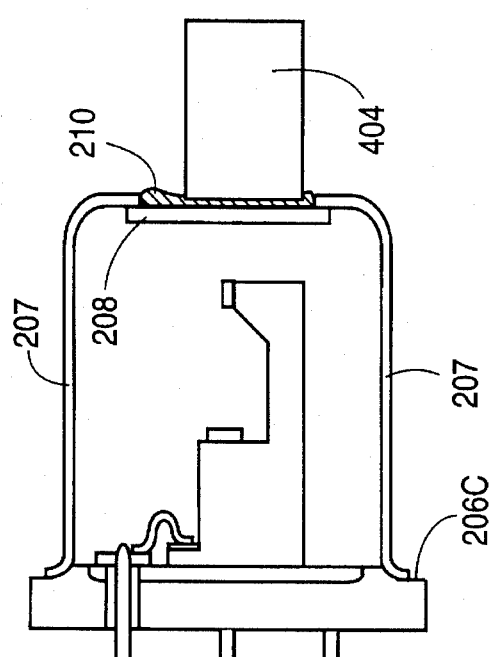
FIGS. 4A, 4B, 4C, 4D, 4E are cross-sectional side views of various embodiments in accordance with the present invention.

FIG. 4A shows another embodiment of a laser diode/lens assembly in accordance with the present invention. In this embodiment, an annular spacer 400 is disposed between biconvex lens 401 and window portion 208. Lens 401 does not necessarily have to be a biconvex lens but rather may be any optical element that is useful in redirecting radiation from a laser diode. Adhesive 210 both fixes spacer 400 to window portion 208 and also fixes spacer 400 to metal can portion 207. Adhesive 210 also fixes lens 401 to spacer 400. Adhesive 210 may or may not be disposed in volume 402 between lens 401 and window portion 208. In the event that adhesive 210 occupies volume 403 between lens 401 and window portion 208, a window portion/gas interface and a gas/lens interface are replaced with a window portion/adhesive interface and a adhesive/lens interface. If the index of refraction of the adhesive is closer to the index of refraction of the window portion and the lens than is the index of refraction of the gas that would otherwise occupy volume 402, then filling volume 402 with adhesive results in more radiation passing through lens 401 and less radiation being reflected back toward the laser diode through window portion 208. In the case of the adhesive filing volume 402, the adhesive in fact becomes a second lens whose curved surface matches that of outer lens surface 401A. It is also possible to construct a lens element whereby spacer 400 is a part of lens element 401. Such a lens/spacer combination would most easily be accomplished in plastic or the like.

Figure 4B:
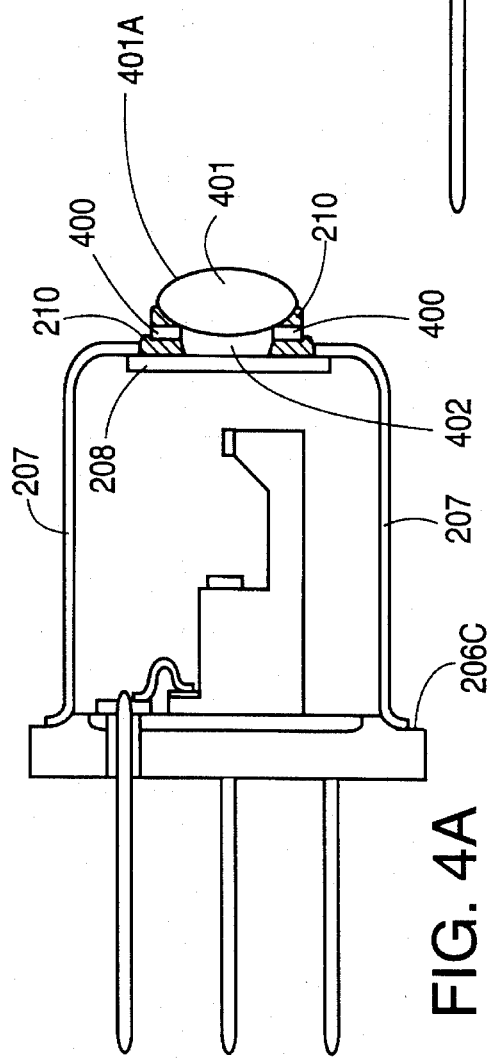
Figure 4C:
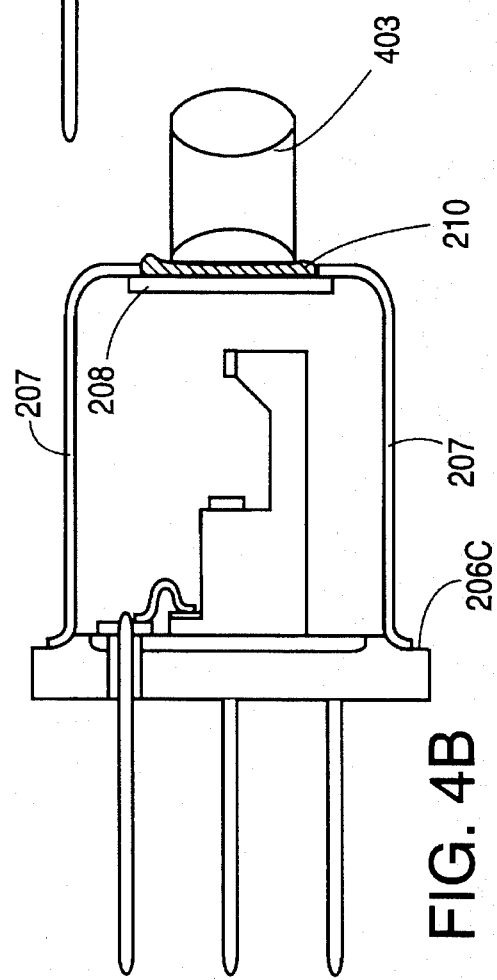

A multi-element lens assembly 403 (see FIG. 4B) or a graded index lens (GRIN) 404 (see FIG. 4C) may also be used to improve output beam quality. Cemented doublets, triplets, or multi-element lens assemblies that are encased in their own mounting hardware such as assembly 405 (see FIG. 4D) may be cemented to housing 207. For best results with multi-element lens assemblies, the more rigidly the elements are attached to each other, the more stable the final laser diode/lens assembly.

Figure 4E:
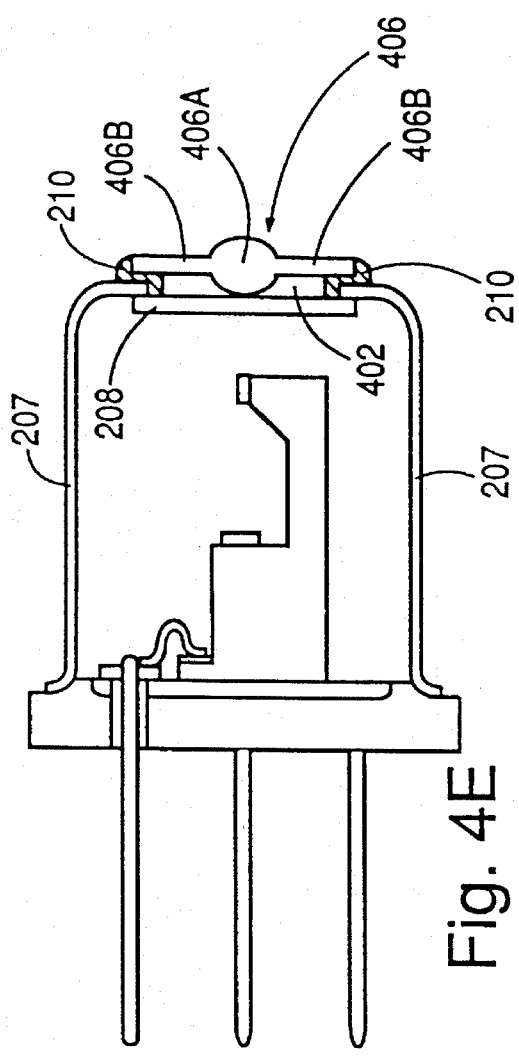
Figure 4D:
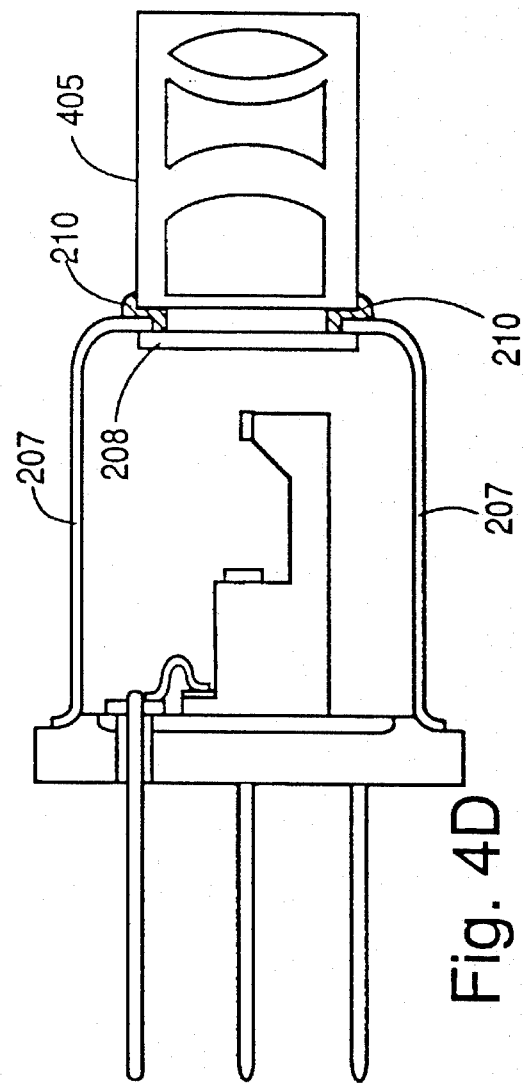

FIG. 4E shows another embodiment of a laser diode/lens assembly of the present invention. In this embodiment, a biconvex lens 406 having a lens portion 406A and an extension portion 406B is employed. Adhesive 210 fixes the extension portion 406B to the window portion 208 and to the metal can portion 207. In some embodiments, adhesive 210 only contacts the metal can portion 207. If adhesive 210 contacts the window portion, it may or may not fill region 402 between lens 406 and window portion 208. The extension portion 460B of the lens may be handled by the micropositioners of a positioning means during handling and orientation of the lens during assembly. Lens 406 does not necessarily have to be biconvex but in general may be any optical element useful for redirecting radiation from a laser diode.

Figure 5:
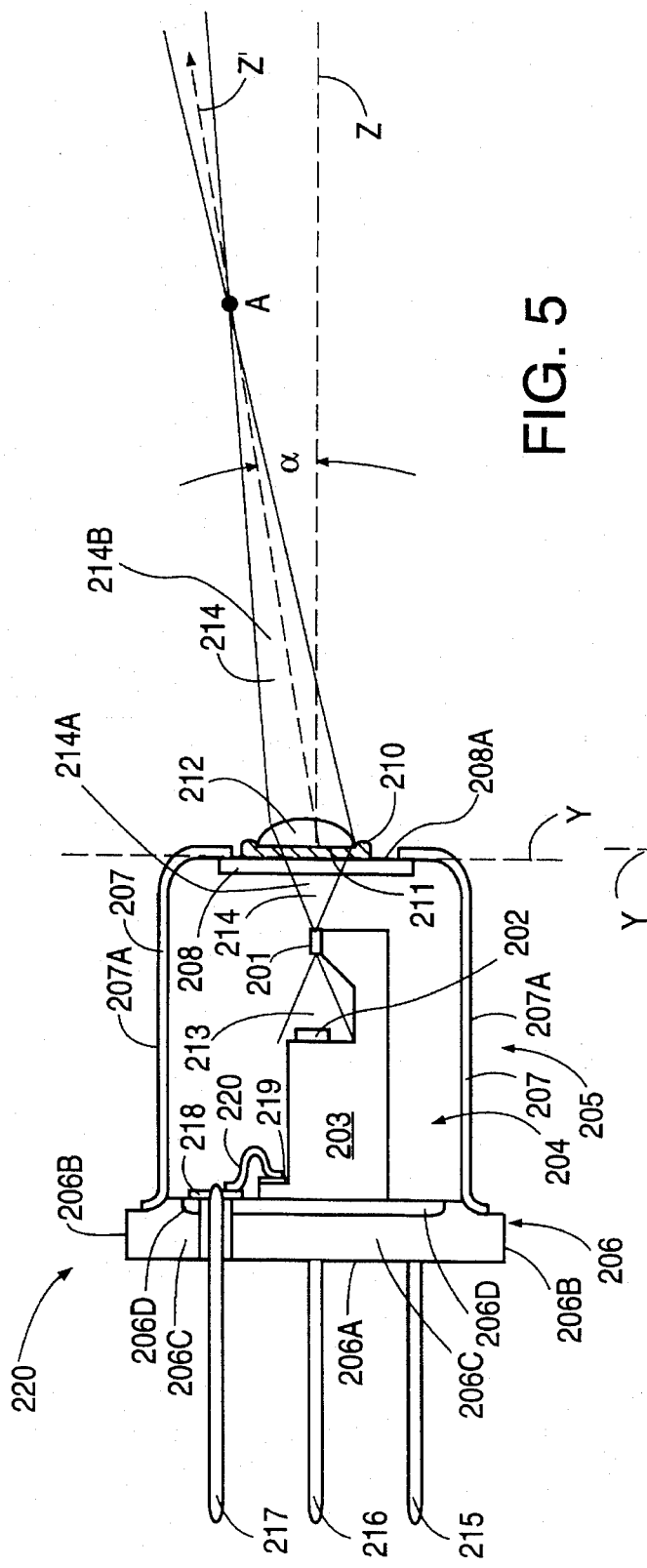
FIG. 5 is a cross-sectional side view depicting a intermediate stage in a method of manufacturing a laser diode/lens assembly in accordance with the present invention.
Figure 6:
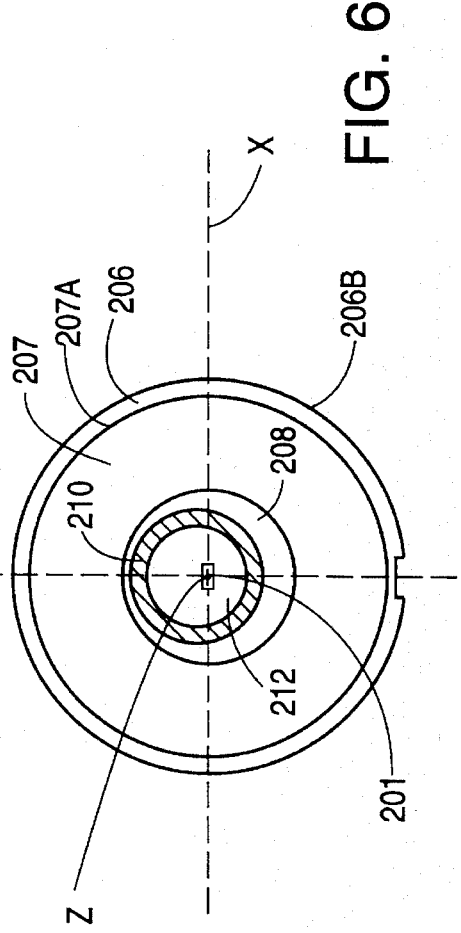
FIG. 6 is a top down view of the intermediate stage of FIG. 5.

FIG. 5 illustrates a step in a method for producing a laser diode/lens assembly in accordance with the present invention. Any laser diode fixed within a housing may be used. A housing such as housing 205 of a laser diode is fixed into a chuck and laser diode 201 inside the housing is turned on by supplying the laser diode with current via the appropriate leads. An amount of uncured adhesive 210 is placed on an outer surface 208A of a window portion 208 of the housing. Adhesive 210 may, for example, be an epoxy which can be rapidly cured by exposure to ultraviolet radiation. One such adhesive is Norland Optical Adhesive #61 produced by Norland Products, Inc., New Brunswick, N.J. 08902. A lens 212 of a suitable size and shape is then placed into the adhesive on the window portion so that a beam 214B of laser radiation is directed along central axis Z' by lens 12. At this stage in the method, lens 212 may be disposed off center with respect to laser diode 201 in the X–Y plane as shown in FIG. 6 so that central axis Z' of beam 214B is out of a desired spatial tolerance with respect to reference axis Z. Using micropositioners, tweezers, or any other convenient means to obtain accurate X–Y movement of lens 212, lens 212 is reoriented in the X–Y plane so that central axis Z' of beam 214B is substantially collinear with reference axis Z or is at a predetermined angle α with respect to reference axis Z. If the final position of lens 212 is at an angle α that is substantially zero, lens 212 may be positioned with respect to the X–Y plane as shown in FIG. 3 so that beam 214B is within the desired angular tolerance as shown in FIG. 2A.

The relative orientation of central axis Z' and reference axis Z may, for example, be determined by monitoring the output of a photodetector positioned along reference axis Z or some other reference axis. With such a setup, lens 212 is properly positioned with respect to the housing 205 when the photodetector detects proper laser radiation from the laser diode. Proper radiation depends upon the type of photodetector used. A simple photodiode might require radiation of a certain magnitude to indicate proper position of lens 212. A quadrant detector would produce balanced outputs from the four detectors to indicate proper position of lens 212. The use of a CCD array camera would necessitate the interpretation either electronically or visually of the output of tens or hundreds of thousands of photodetectors. Such methods as have been described together with others not mentioned are known in the art of beam positioning and detecting.

Once the lens is properly positioned so that angle α is acceptable, lens 212 is "frozen" in place by curing adhesive 210. In the event the adhesive is Norland Optical Adhesive #61, the adhesive may be cured by exposing the adhesive to ultraviolet radiation in the range 320–400 nm for a time duration dependent upon the intensity and wavelength of the ultraviolet light source.

The result of this manufacturing method is a laser diode/lens assembly having a lens which is immovably fixed to a laser diode housing. Accordingly, the lens of the laser diode/lens assembly of the present invention is more resistant than conventionally mounted lenses to disalignment caused by mechanical shocks, thermal stresses, and mechanical vibrations. Additionally, because the present invention in one embodiment uses only one relatively inexpensive lens in comparison to complex conventional lens and mounting assemblies employing multiple relatively expensive lenses and prisms and, further, because there is no hardware, other than epoxy and possibly a spacer, which connects the lens to the laser housing, the present invention results in significant cost savings over conventional laser diode lens mounting techniques.

Figure 7:
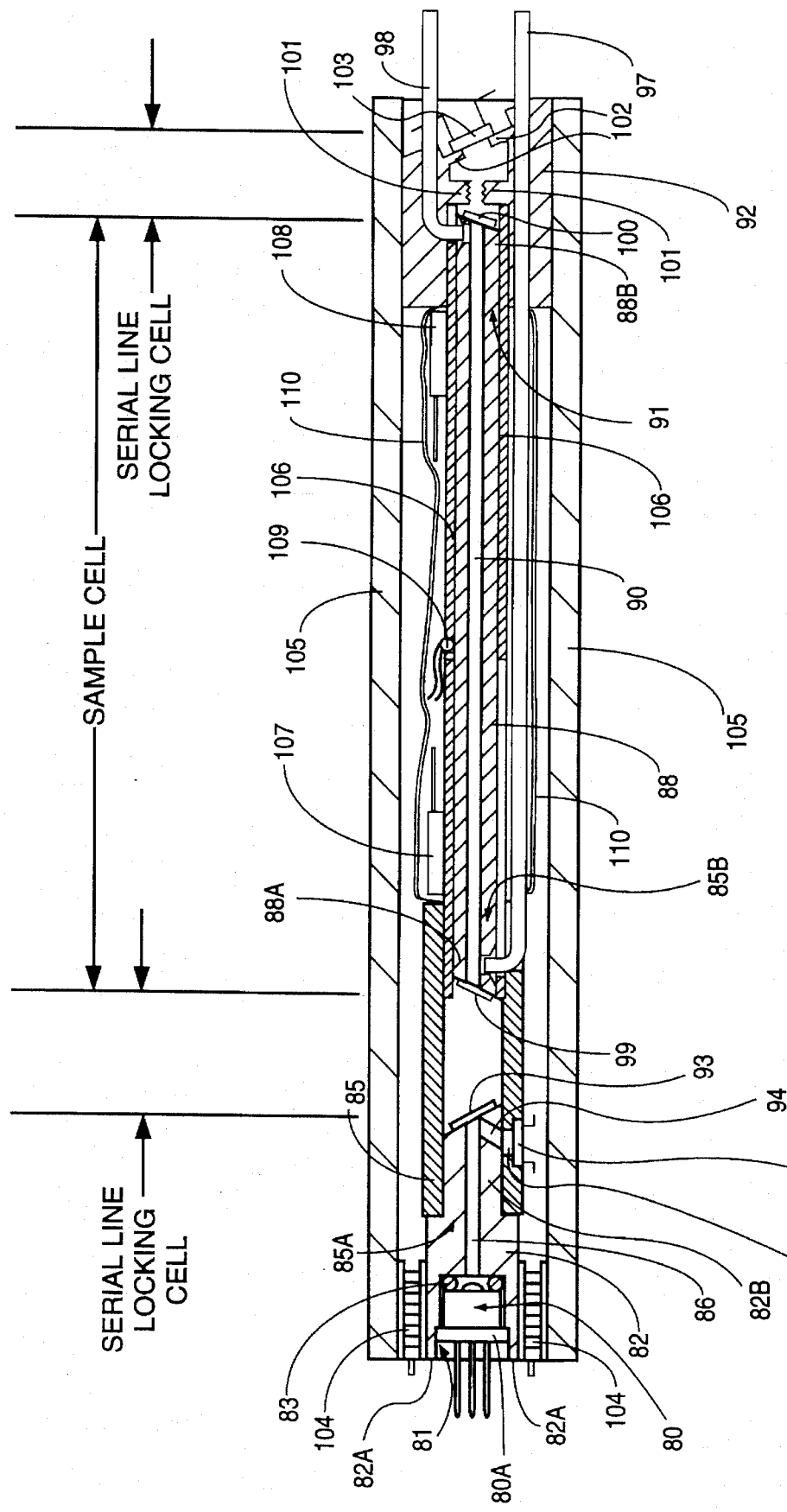
FIG. 7 is a cross-sectional view of a gas spectroscopy device employing a serial line locking cell and incorporating a laser diode/lens assembly.

FIG. 7 is a cross-sectional view of a gas spectroscopy device comprising a laser diode/lens assembly. A planar reference surface of base portion 80A of laser diode/lens assembly 80, previously referred to in FIG. 2 as surface 206C, is pressure fitted into cylindrical mounting opening 81 in first end 82A of laser mounting member 82 until the laser diode housing compresses rubber o-ring 83 and a ledge reference surface of base portion 80A is pressed against and therefore spatially referenced to an inside ledge surface 206C of laser mounting opening 81.

A second end 82B of laser mounting member 82 is disposed in first end 85A of joining tube member 85. A beam splitter 93 is disposed on the end 82B of laser mounting member 82 so that a portion of a laser radiation beam emitted from laser/diode lens assembly 80 is reflected through monitor hole 94 in the laser mounting member 82, through monitor hole 95 in joining tube member 85, and to a photodetector 96 which is fixed at an angle on the joining tuber member 85.

A first end 88A of a sample cell tube member 88 is disposed in second end 85B of joining tube member 85 so that axial hole 90 in sample cell tube member 88 is aligned with axial hole 86 in the laser mounting member 82. Sample cell tube member 88 may, for example, be made of a plastic material. In the preferred embodiment sample cell tube 88 is fabricated from glass capillary tubing obtained from Schott Glass, PN#31140876 which has a 8.380±0.2 mm outside diameter and a 1.575±0.013 mm inside diameter. The small diameter of the axial hole 90 in the sample cell tube member 88 allows measurements of oxygen concentration to be made quickly upon the introduction of only a small volume of sample gas into the axial hole 90.

A second end 88B of sample cell tube member 88 is disposed in receiving opening 91 of a photodetector holding member 92. A first window 99 is disposed on end 88A of the sample cell tube member 88 and a second window 100 is disposed on end 88B of the sample cell tube member 88 in order to seal the axial hole 90 of the sample cell tube member 88 to create a sample cell. An end of a metal input tube 97 is disposed in a hole in sample cell tube member 90 and an end of a metal output tube 98 is disposed in another hole in sample cell tube member 90 so that sample gas can flow into the sample cell through input tube 97, flow through axial hole 90, and can be exhausted from the sample cell through output tube 98.

In the preferred embodiment, photodetector holding member 92 comprises a tube portion 101 as well as a radiation trap portion 102. A photodetector 103 is fixed to photodetector holding member 92 in such a position that a beam of laser radiation emitted from laser diode/lens assembly 80 passes through axial holes 86 and 90, passes through tube portion 101, passes through radiation trap portion 102, and is incident on photodetector 103. The inside surface of tube portion 101 has a rough surface to attenuate laser radiation which otherwise might pass back through tube volume 101 after being reflected off photodetector 103 and then being reflected off the inside surface wall of tube portion 101. The radiation absorbing rough inside surface of the tube portion 101 tends not to reflect laser radiation back into the axial hole 90. Radiation trap portion 102 is provided to attenuate laser radiation which is reflected off the photodetector 103 but which does not reflect with an appropriate angle to pass directly into the tube portion 101. The structure of the radiation trap portion serves to cause much of this laser radiation to reflect off multiple radiation absorbing inside surfaces of the radiation trap portion 102 before this laser radiation obtains a appropriate direction to pass into tube portion 101. The radiation trap portion therefore serves to attenuate laser radiation before it enters tube portion 101. In some embodiments, a tube portion is provided with no trap portion.

Not only does the structure of FIG. 7 have a sample cell, but the structure of FIG. 7 has a serial line locking cell disposed in series with the sample cell. The line locking cell contains a reference gas to which is used to lock the frequency of the laser radiation emitted from the laser diode/lens assembly 80 to a spectral line of the reference gas in the serial line locking cell. If the sample gas in the sample cell is used to lock onto a spectral line, the device cannot measure low sample gas oxygen concentrations in the range of approximately 0–5%. The device of FIG. 7, on the other hand, locks onto a reference gas known to be in the serial line locking cell and therefore can be locked to detect sample gas concentrations in the sample cell down to approximately 0%. Moreover, by placing both the reference gas and the sample gas on the same axis of a laser beam, the expense of the spectroscopy device is reduced and the resulting spectroscopy device can be made more compact.

In the embodiment illustrated in FIG. 7, the reference gas to which the laser radiation is locked is present in the volume between beam splitter 93 and window 99 of the sample cell tube member 88 as well as in the volume between window 100 and photodetector 103 in the photodetector holding member 92. In some embodiments, the serial line locking cell is open to ambient air. In other embodiments, the serial line locking cell is supplied with a reference gas other than ambient air. In some embodiments, the serial line locking cell is sealed with a reference gas which contains relatively little water vapor and which has a known gas constituent concentration. In some embodiments, the pressure and/or temperature of the reference gas may be controlled.

To prevent laser radiation reflected off the beam splitter 99, the first and second windows 99 and 100, and the photodetector 103 from being reflected back into the laser diode, the beam splitter 99, the first and second windows 99 and 100, the photodetector 103 are each positioned at an angle with respect to the axis of the beam of laser radiation which passes from the laser diode/lens assembly to the photodetector 103. Reflections off these structures therefore tend to be attenuated.

The beam of laser radiation emitted from laser diode/lens assembly 80 need not be highly collimated because most of the non-collimated radiation which enters the serial line locking cell and the sample cell is reflected down axial holes 86 and 90 at grazing incidence and is received by photodetector 103. In the embodiment shown in FIG. 7, photodetector 103 is located approximately 6.5 inches from the lens of the laser diode/lens assembly. In the embodiment of FIG. 7, the lens of the laser diode/lens assembly is positioned in the X–Y plane so that the central axis of the beam which is output by the laser diode is within a tolerance of 0 to 0.3 degrees to an axis, where the axis is normal with respect to the reference ledge surface 206C of the laser diode/lens assembly 80.

In operation, laser diode/lens assembly 80 generates a semi-collimated beam of laser radiation which passes through the reference gas in the serial line locking cell, through the sample cell, through the remainder of the serial line locking cell, and to photodetector 96. Photodetectors 103 and 96 are used to differentially determine the amount of absorption of laser radiation which occurs in the sample cell. Because the frequency of radiation emitted from a laser diode is dependent upon the temperature of the laser diode itself, the frequency of the beam of laser radiation emitted from laser diode/lens assembly 80 is controlled to be locked onto a spectral line of the reference gas in the serial line locking cell by controlling the temperature of the laser diode.

Figure 8:
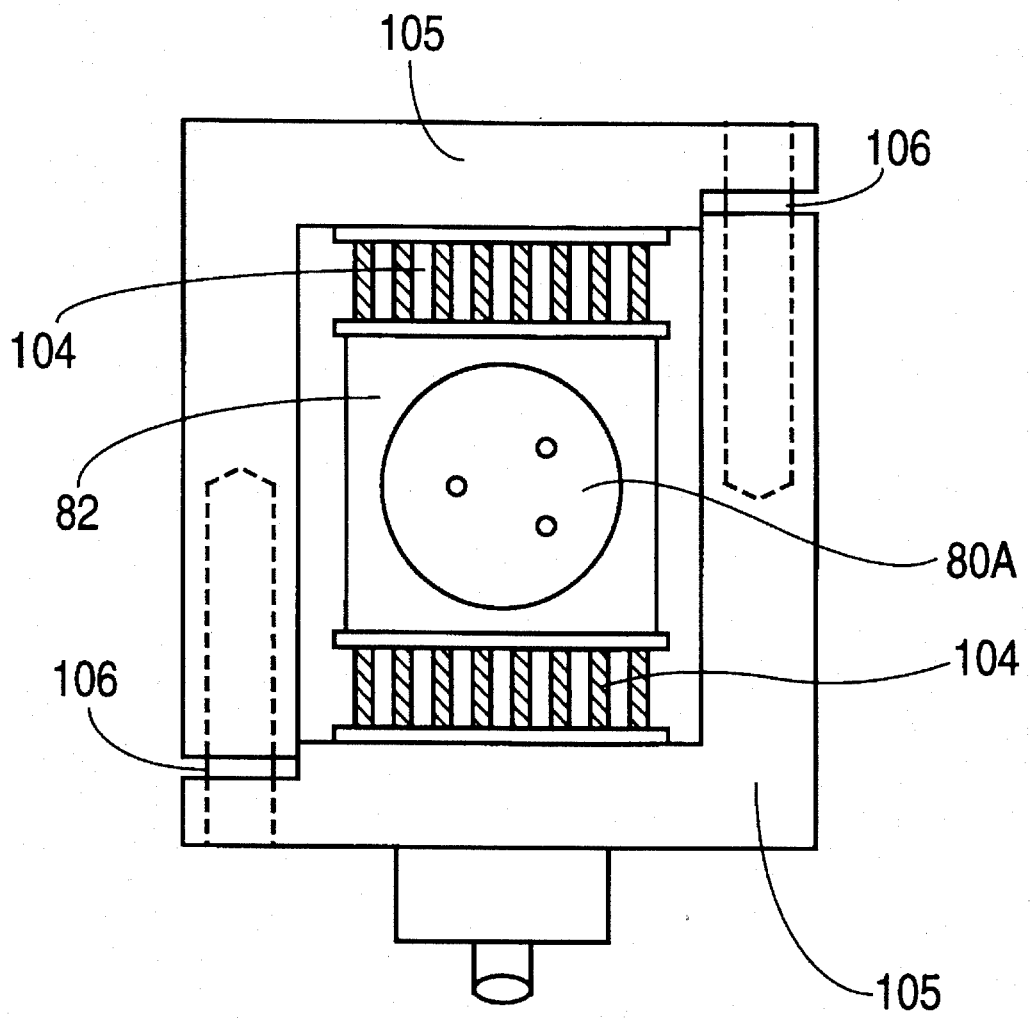
FIG. 8 is an end view of the gas spectroscopy device of FIG. 7.

FIG. 8 is an end view of the gas spectroscopy device of FIG. 7. A rough temperature adjustment of laser diode temperature is accomplished using a pair of thermoelectric coolers 104 which are disposed between laser mounting member 82 and two respectively thermally conductive support members 98 which function as a heat sink. In the embodiment of FIGS. 7 and 8, support members 105 have an angled shape and are joined by screws 106 so that the two thermoelectric coolers 104 are held pressed against the laser mounting member 82 and are pressed against the support members 105. Laser mounting member 82 is made of thermally conductive material such as a metal so that the thermoelectric coolers can efficiently and accurately cool the laser diode inside the laser mounting member 82. Heat from the laser diode/lens assembly base portion 80A is removed from the diode inside the laser diode/lens assembly via the thermoelectric coolers and radiated away via the thermally conductive support members 105. Support members 105 also function to hold the photodetector holding member 92 in a stable position with respect to laser mounting member 82 so that the laser diode/lens assembly, the two parts of the serial line locking cell, the sample cell, and photodetectors remain in proper alignment. Fine temperature adjustment of diode temperature is performed by controlling the magnitude of Current supplied to the laser diode.

Because one application of the gas spectrometry device of FIG. 7 involves the analysis of human breath and more specifically involves determining the oxygen concentration in human breath, the sample cell is heated to avoid water vapor in human breath from condensing on windows 99 and 100 and on the inside surface of axial tube 90. Moreover, the spectral characteristics of a gas being analyzed may change as a function of temperature. A thermally conductive sheath 106 is therefore placed around sample cell tube member 88 and transistors 107 and 108 are placed in thermal contact with the sheath so that the sheath 106 can be heated by the transistors to a controlled temperature based on a temperature detected by thermistor 109. A covering 110, which in the preferred embodiment is a heat shrink covering, is used to maintain the sample cell tube member 88 in the same thermal environment as the temperature-controlled sheath and the input tube 97. Joining tube member 85 is therefore made of a thermally nonconductive material such as plastic or the like so that the temperature of this part of the sample cell can be maintained at a temperature which is different from the temperature of the laser mounting member 82 and laser diode. With this construction, human breath passing into the sample cell at a flow rate of 150 ml/minute through an input tube 97 having a diameter of 1/16 inches is heated during its passage through the heated input tube 97 to a temperature adequately close to the temperature of the windows 99 and 100 such that water vapor in human breath does not condense inside the sample cell.

Figure 9:
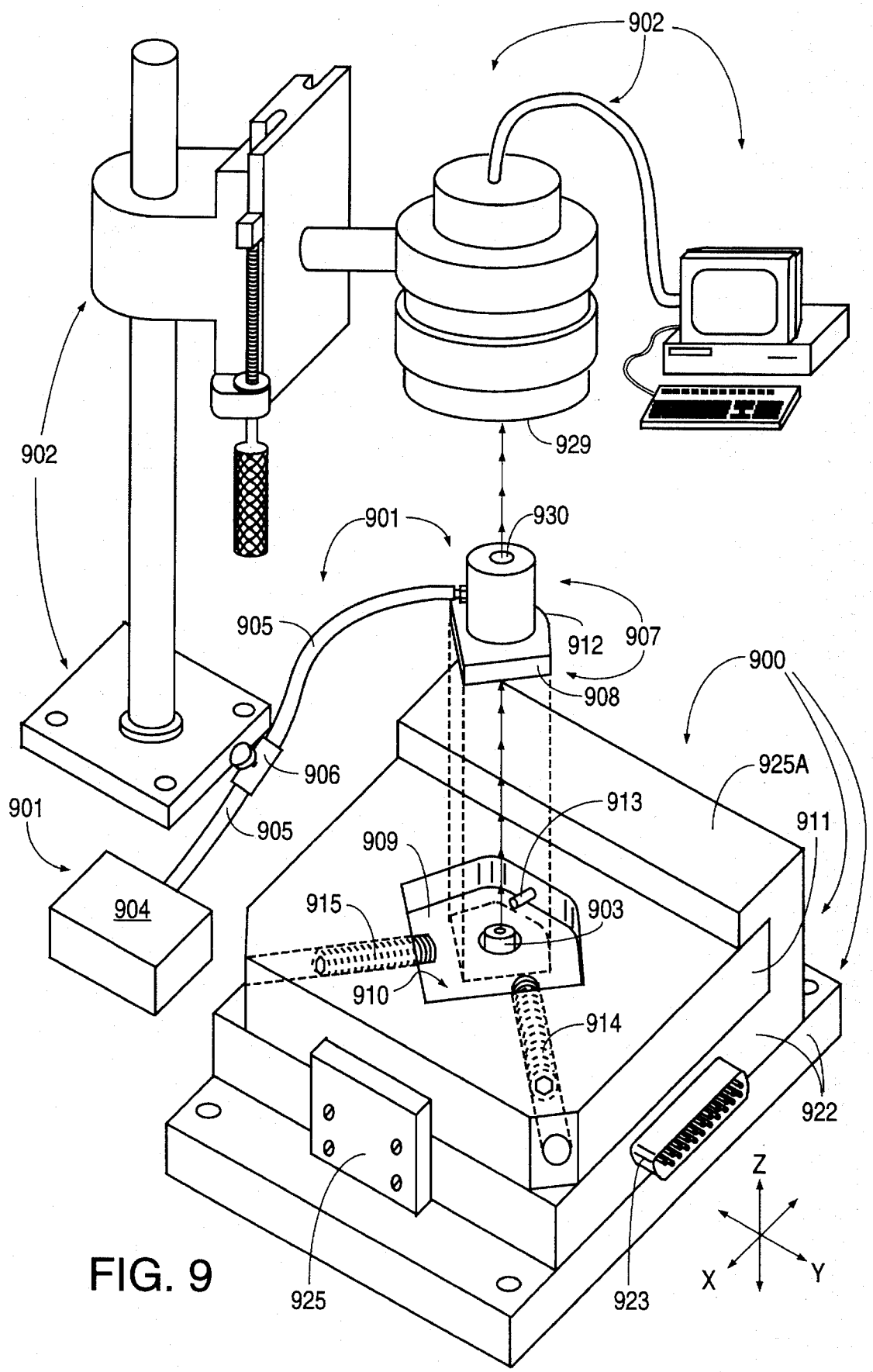
FIGS. 9, 10, 10A, 11, 12, 13, 14 are diagrams illustrating specific embodiments in accordance with the present invention wherein a lens is positioned and fixed in three dimensional space with respect to laser diode housings.

FIG. 9 is a perspective view in accordance with an embodiment of the present invention in which a lens is positioned in three dimensions (X, Y and Z) and then immovably fixed in three dimensional space with respect to a laser diode housing. The structure of FIG. 9 comprises a laser diode housing holding member 900, a lens holding member 901, and a beam detecting device 902. A laser diode housing 903 is shown being held by laser diode housing holding member 900 so that laser radiation emitted from a laser diode inside housing 903 passes upward to beam detecting device 902. Lens holding member 901 comprises a vacuum pump 904, a vacuum tube 905, a pressure regulating valve 906, and a movable partial vacuum chamber member 907. A base plate 908 of partial vacuum chamber member 907 slides in the X–Y plane on surface 909 in an opening 910 in top plate 911 of the laser diode housing holding member 900. A side edge 912 on the back of base plate 908 engages a spring pin 913 such that partial vacuum chamber member 907 is easily moved in the X–Y plane by two screws 914 and 915.

Figure 10:
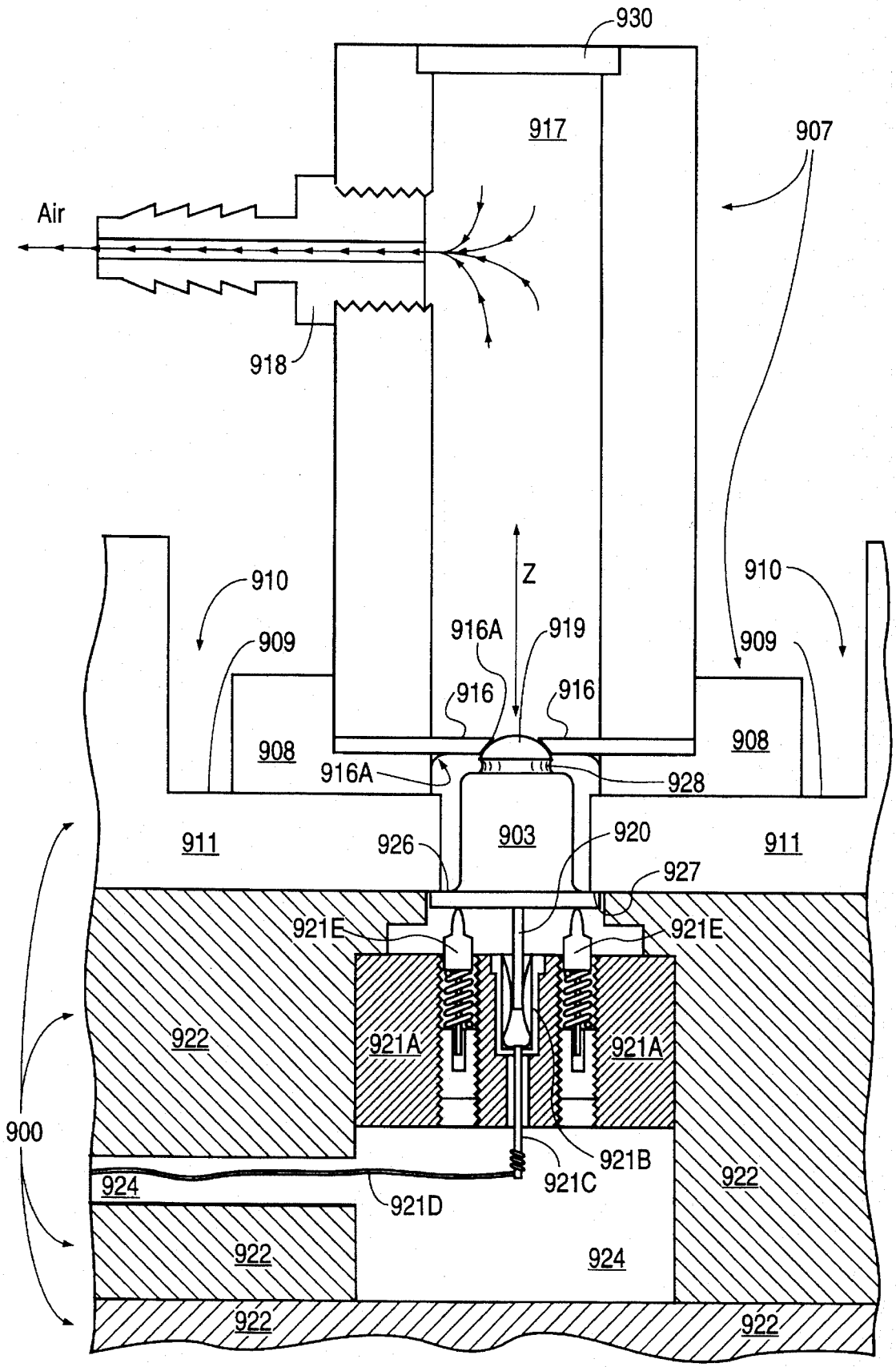

FIG. 10 is a cross sectional view showing partial vacuum chamber member 907 disposed in opening 910 such that the bottom of base plate member 908 slidably engages the top surface 909 of the laser diode housing holding member 900. Loctite 290 adhesive 916A fixes a flexible membrane 916 in place to base plate 908. Air is evacuated from partial vacuum chamber 917 through vacuum tube coupling 918, vacuum tube 905, pressure regulating valve 906 and vacuum pump 904 such that a lens 919 is grasped in a central circular opening of washer-shaped flexible membrane 916.

Figure 10A:
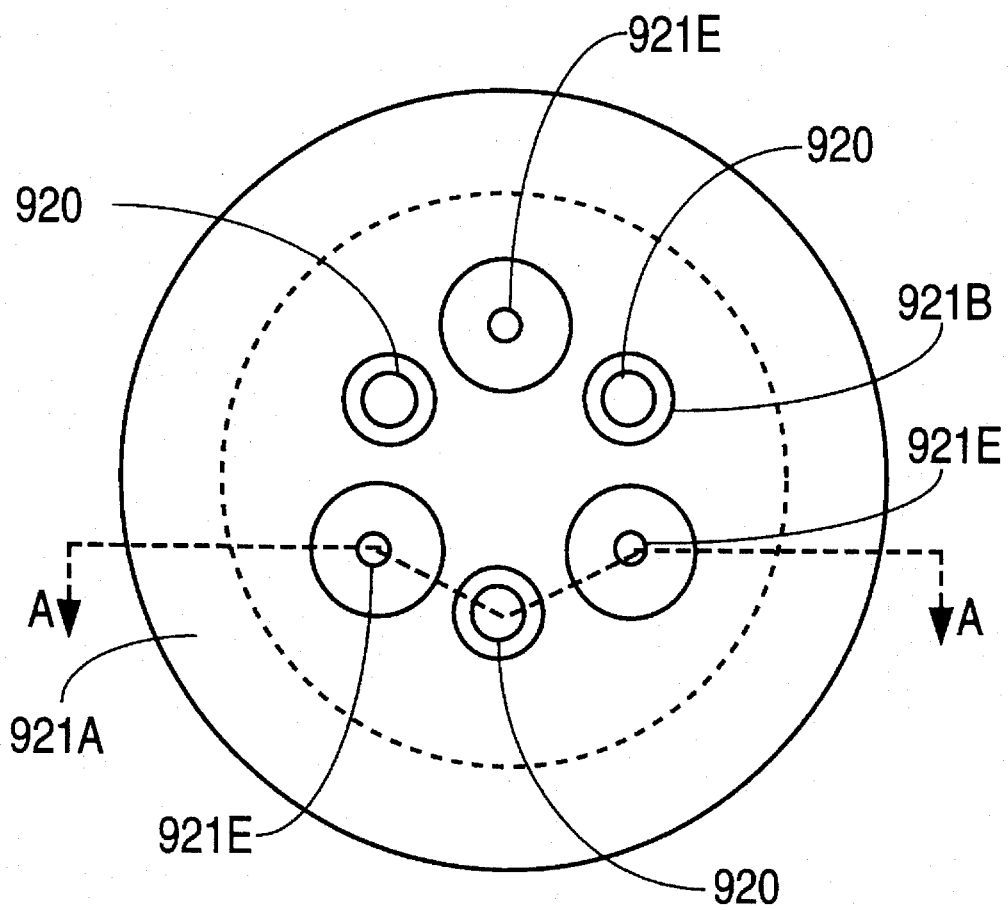

FIG. 10A is a top-down view of a socket 921 disposed in an opening in bottom member 922 of the laser diode housing holding member 900. The sectional line A—A indicates where the cross-sectional view of FIG. 10 is taken. FIG. 10 shows in cross section one of three leads 920 of laser diode housing 903 coupled in one of three corresponding Auget lead sockets 921B of socket 921. As shown in the top-down view of FIG. 10A, the three lead sockets 921B are disposed in a configuration to accommodate the lead pattern of the laser diode housing. An electrical connection is maintained from the laser diode lead 920, through the Auget lead socket 921B, through socket lead 921C, through wires 921D, and to an external connector 923. A chamber 924 is provided in the laser diode housing holding member 900 to accommodate wires 921D.

To place the laser diode housing 903 in the laser diode housing holding member 900, a top member 911 of the laser diode housing holding member is removed from a bottom member 922 of the laser diode housing holding member. The laser diode housing 903 is then pressed downward into socket 921 so that a bottom surface of the laser diode housing 903 nears or engages the top surface of socket member 921A of socket 921. An edge of the top member 911 of the laser diode housing holding member 900 is then slid under the L-shaped bracket portion 925A of the bottom member 922 and the top member 911 is locked in place with a locking plate 925 so that a top surface 926 of laser diode housing 903 is pressed upward by spring screws 921E to contact a bottom surface 927 of top member 911 of laser diode housing holding member 900. Lens 919 is placed into the central opening in flexible member 916 of the partial vacuum chamber member 907 with vacuum pump 904 energized and valve 906 opened partially. The partial vacuum in partial vacuum chamber 917 holds lens 919 in place in the opening in flexible member 916. With lens 919 so held, an amount of UV curable adhesive 928 is placed on the bottom surface of lens 919 and the partial vacuum chamber member 907 is placed down over the top of laser diode housing 903 such that the uncured adhesive contacts the upper surface of the housing 903. With base plate 908 of the partial vacuum chamber member 907 resting on surface 909 inside opening 910 of the laser diode housing holding member 900, screws 914 and 915 are manipulated to move the lens in the X–Y plane such that a beam of laser radiation emitted from the laser diode in housing 903 is aligned to be within some desired angle α of the Z axis. Beam detecting device 902 detects where in the X–Y plane this beam is incident upon a detector 929. The partial vacuum chamber member 907 has a window 930 which allows the beam of laser radiation to pass to the detector 929.

Not only can lens 919 be positioned in the X–Y plane, but lens 919 can also be positioned in the Z dimension. To position lens 919 farther away from housing 903, for example, the partial vacuum in partial vacuum chamber 917 is increased and then fixed by valve 906, thereby flexing flexible member 916 upward and maintaining it so flexed. Similarly, to position lens 919 farther towards housing 903, the partial vacuum in partial vacuum chamber 917 is lessened, thereby flexing flexible member 916 less and disposing lens 919 closer to the housing 903. A focal point of the laser radiation is adjusted in accordance with one embodiment by varying the distance between lens 919 and housing 903 such that a desired spot size is detected on detector 929. With lens 919 properly positioned in the X, Y and Z dimensions, the beam detecting device 902 is pivoted away from above window 930 and a source of UV radiation (not shown) emits laser radiation downward through window 930 and through lens 919 such that UV curable adhesive 928 cures. Lens 919 is thereby permanently fixed in a desired position to laser diode housing 903.

Figure 11:
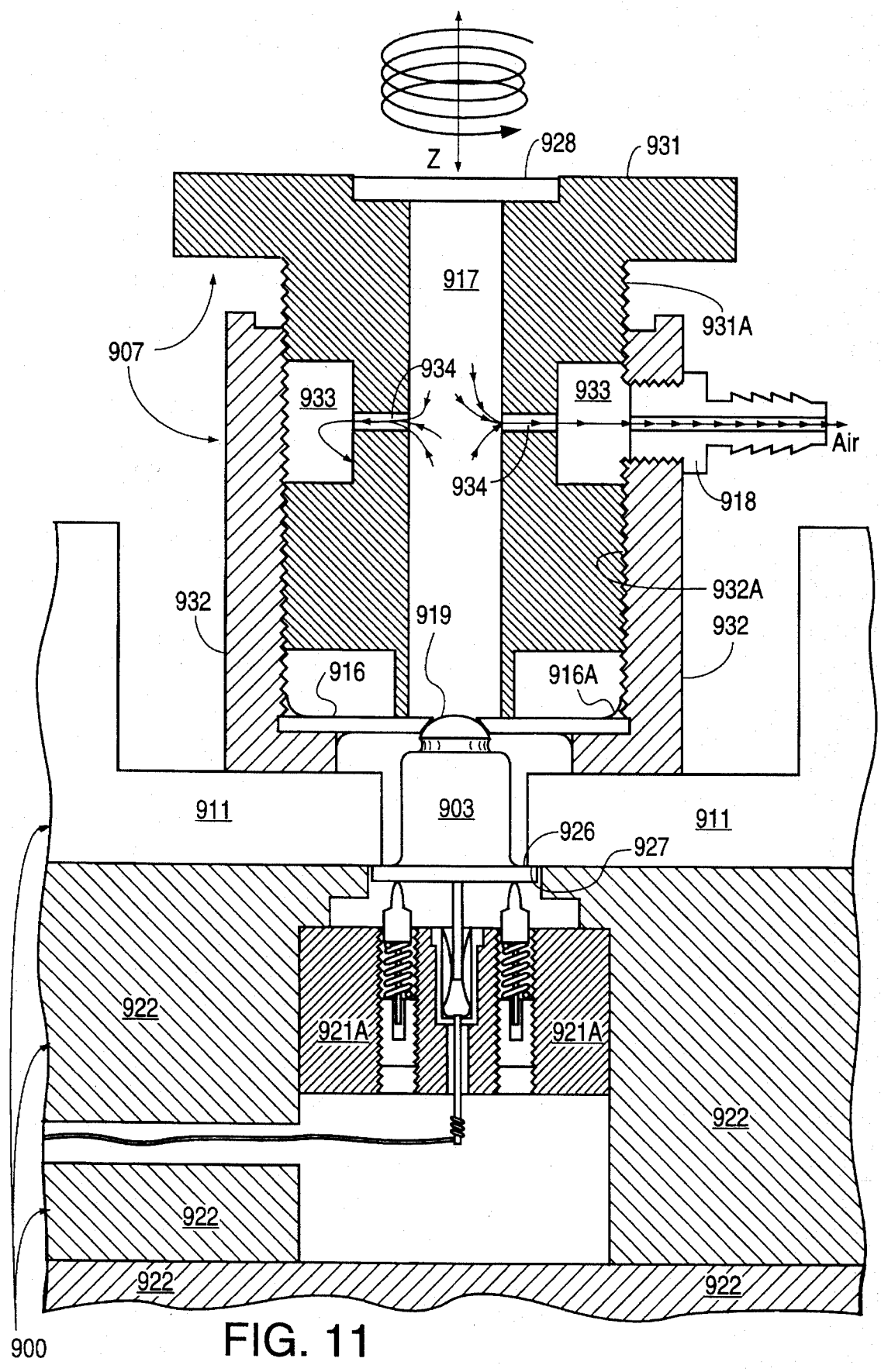

FIG. 11 is a cross sectional view of another embodiment in accordance with the present invention in which partial vacuum chamber member 907 comprises a first portion 931 and a second portion 932. First portion 931 is rotatable with respect to second portion 932 via threads 931A and 932A such that lens 919 is movable up and down in the Z dimension depending on the amount that first portion 931 pushes flexible member 916 downward. Vacuum tubing 905 of FIG. 9 is coupled to vacuum tube coupling 918 to provide a partial vacuum chamber member 907. A circular groove 933 and inwardly extending holes 934 in first portion 931 allow air to be withdrawn from partial vacuum chamber 917 through coupling 918 when first portion 931 is being rotated.

Figure 12:
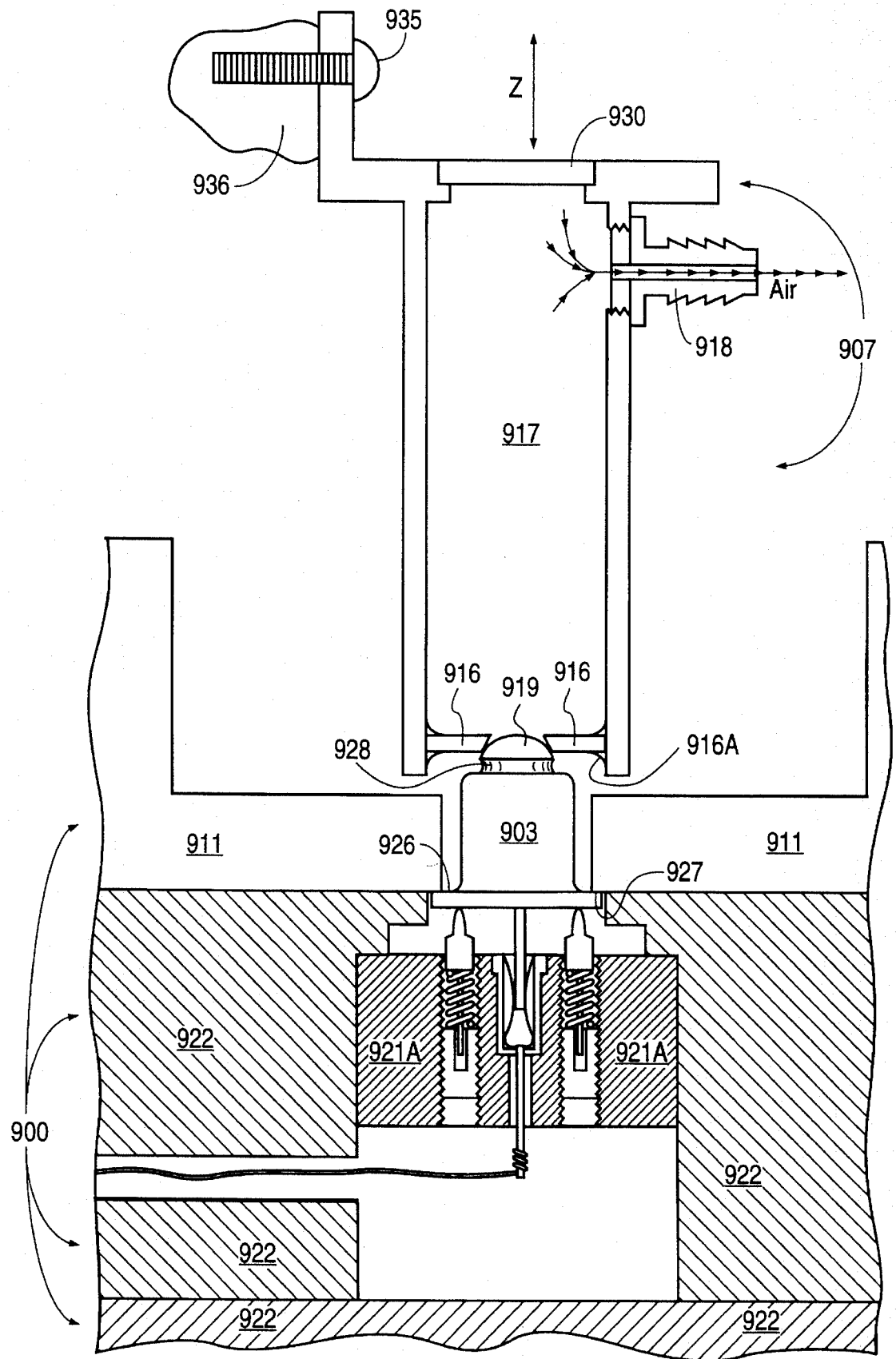

FIG. 12 shows yet another embodiment in accordance with the present invention. In this embodiment, partial vacuum chamber member 907 does not have a base plate 908 which slides on upper surface 909. Rather, partial vacuum chamber member 907 is removably fixed by a suitable means such as screw 935 to a three axis micropositioner 936. Lens 919 can therefore be moved in the X, Y and Z dimensions when the UV curable adhesive is still uncured. The UV curable adhesive 928 is cured via window 930 once the lens is properly positioned.

Figure 13:
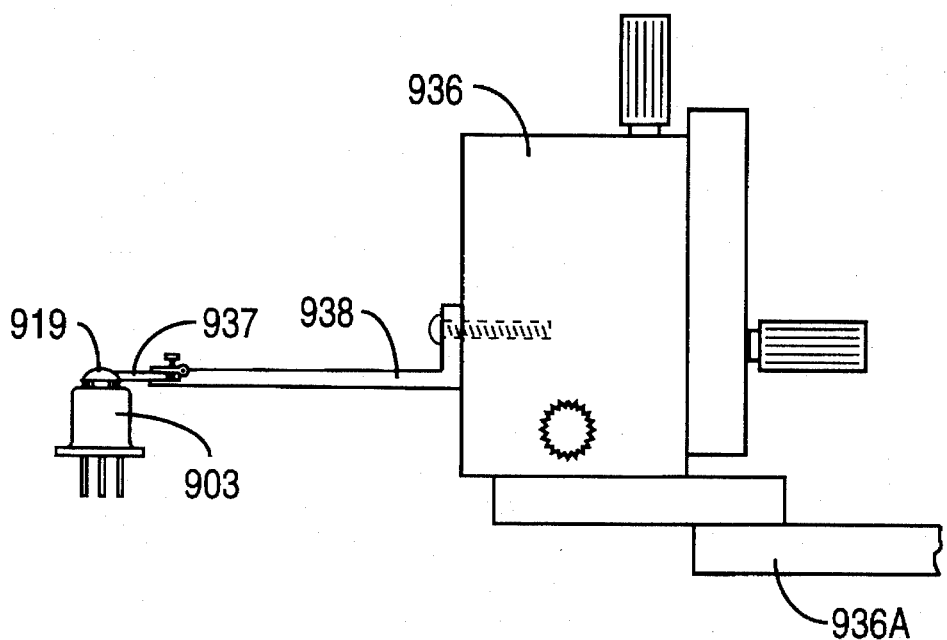
Figure 14:
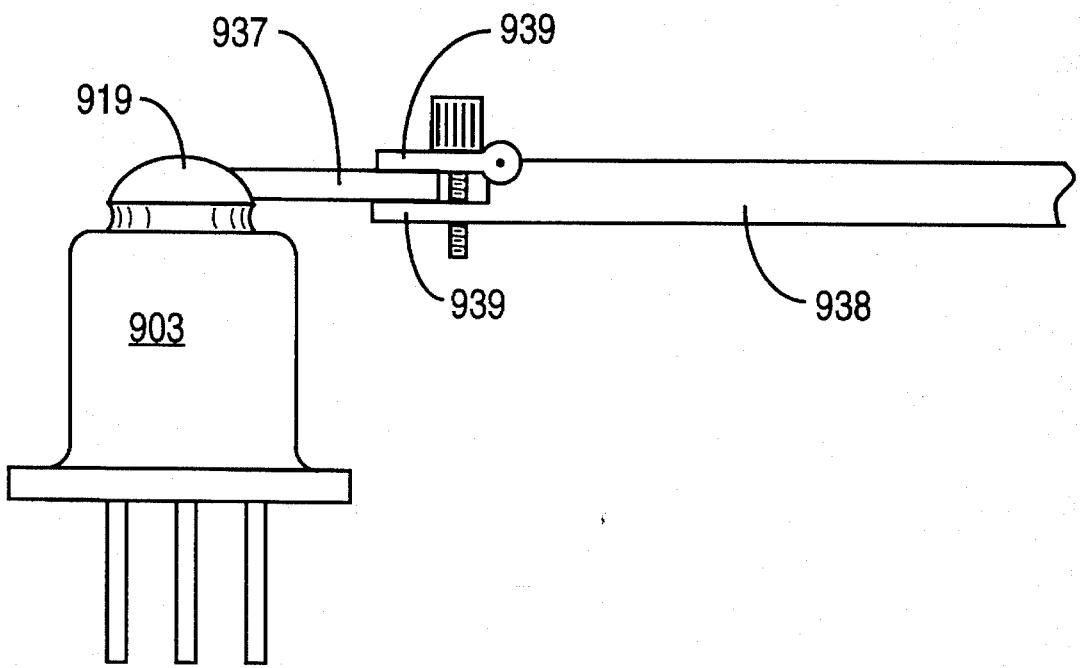

FIGS. 13 and 14 show yet another embodiment in accordance with the present invention. In this embodiment, lens 919 is optionally provided with a gripping extension 937. This gripping extension 937 may be clipped or otherwise removed from lens 919 after the adhesive is cured and lens 919 is fixed in a desired position with respect to housing 903. A plastic gripping extension may be integrally formed with a plastic lens. A gripper arm 938 may be coupled to three axis micropositioner 936, the gripping extension 937 being clamped onto the gripping arm 938 by jaws 939. It is to be understood, however, that any suitable means of grasping lens 919 so that lens 919 can be positioned in the X, Y and Z dimensions with a micropositioner may be used. Housing 903 is removably fixed with respect to mounting portion 936A of micropositioner 936 so that lens 919 may be positioned in the X, Y and Z dimensions using a beam detecting device 902 such as shown in FIG. 9. Any suitable type of lens may be positioned and fixed in three dimensional space with respect to laser diode housing 903 in accordance with the invention. The adjusting and fixing of the lens position in three dimensional space with respect to a laser diode housing may be automated if desired for mass production. In one embodiment, beam detecting device 902 is a Beam Scan model 2180 Optical Profiles model, obtainable from Photo, Inc., 1115 Space Park Drive, Santa Clara, Calif. 95054 and three axis micropositioner 936 is a MT-XYZ or 5610-XYZ model, obtainable from Newport Corp., 1791 Deere Avenue, Irvine, Calif. 92714.

Although the present invention has been described in connection with certain exemplary embodiments, the present invention is not limited thereto. The present invention is not limited to metal can style laser diode housings. The housing need not to be hermetically sealed. One lens or multiple lenses may be fixed to another type of laser diode housing in accordance with the present invention. A lens may be fixed to a window portion of a housing, to another portion of a housing, or to both. The use of the laser diode/lens assembly of the present invention in gas spectrometry may result in a significant cost savings. Numerous embodiments other than the specific embodiments illustrated for positioning and fixing a lens in three dimensional space with respect to a laser diode housing may be practiced in accordance with the present invention. The invention is not limited to require socket 921 and surface 927. Rather, other suitable structures for supplying power to the diode inside a laser diode housing when the laser diode housing is in a fixed position may be employed. It is to be understood, therefore, that various changes, modifications, and adaptations of the above described embodiments may be practiced without departing from the spirit and scope of the invention as set forth in the appended claims.

What is claimed is:

1. A method, comprising:

moving a lens into a position with respect to a laser diode housing such that a minimum distance between said laser diode housing and said lens changes during said moving, an amount of uncured adhesive being in contact with both said lens and said housing during said moving; and after said moving, curing said adhesive to fix said lens in said position with respect to said housing.

2. The method of claim 1, wherein said lens is moved in a direction Z substantially collinear with an axis of a beam of laser radiation, said beam of laser radiation being emitted from a laser diode disposed inside said laser diode housing.

3. The method of claim 2, wherein said lens is also moved in a second direction substantially perpendicular to said direction Z when said amount of uncured adhesive is in contact with both said lens and said housing.

4. The method of claim 1, further comprising:

grasping said lens using a partial vacuum.

5. The method of claim 4, wherein said moving involves:

moving said lens with respect to said laser diode housing using a micropositioner.

6. The method of claim 1, further comprising:

gripping a gripping extension of said lens.

7. The method of claim 6, wherein said moving involves:

moving said lens with respect to said laser diode housing using a micropositioner.

8. The method of claim 1, wherein said moving involves detecting a location where a beam of laser radiation is incident upon a detector, said beam of laser radiation passing from inside said laser diode housing, through said lens, and onto said detector.

9. The method of claim 8, wherein said lens is moved with respect to said laser diode housing until said location has a desired spatial relationship with respect to said laser diode housing.

10. The method of claim 1, wherein said moving involves moving said lens with respect to said laser diode housing until a spot size of laser radiation detected on a detector has a desired area, said laser radiation passing from inside said laser diode housing, through said lens, and onto said detector.

11. Structure for positioning a lens with respect to a laser diode housing when said lens is disposed in an amount of uncured adhesive, comprising:

a laser diode housing holding member, said laser diode housing holding member being adapted to removably hold said laser diode housing;

a lens holding member, said lens holding member being controllable to move said lens with respect to said laser diode housing member in the three dimensions (X, Y and Z) of three dimensional space when said uncured adhesive is in contact with both said lens and said laser diode housing, said lens holding member being adapted to be disengaged from said lens after said amount of uncured adhesive is cured; and a beam detecting device disposed to detect laser radiation emitted from a laser diode disposed inside said laser diode housing while said lens holding member is in contact with said lens but before said amount of uncured adhesive is cured.

12. The structure of claim 11, wherein said lens holding member has a window through which said laser radiation passes.

13. The structure of claim 12, wherein said lens holding member has a partial vacuum chamber.

14. The structure of claim 11, wherein said lens holding member comprises a three-axis micropositioner.

15. The structure of claim 12, further comprising an ultraviolet radiation source disposed to expose said amount of uncured adhesive to ultraviolet radiation, said amount of adhesive being cured by ultraviolet radiation passing through said window.

16. The structure of claim 11, wherein said laser diode housing holding member comprises electrical conductors for supplying electrical power to said laser diode when said lens is being moved with respect to said laser diode housing.

17. Structure, comprising:

means for moving a lens with respect to a laser diode housing, said lens moving in the three dimensions (X, Y and Z) of three dimensional space, an amount of uncured adhesive contacting both said lens and said laser diode housing during said moving; and a beam detecting device detecting laser radiation emitted from a laser diode disposed inside said laser diode housing when said adhesive is uncured.

18. The structure of claim 17, wherein said laser diode housing has a window, said window having an outside surface disposed in a plane, said dimensions X and Y defining said plane, said dimension Z being perpendicular to said plane.

* * * * *